United States Patent
Zajac

(10) Patent No.: US 9,795,392 B2
(45) Date of Patent: Oct. 24, 2017

(54) SURGICAL INSTRUMENTATION SET AND SURGICAL TECHNIQUE

(71) Applicant: Arthrex, Inc., Naples, FL (US)

(72) Inventor: Eric Zajac, Naples, FL (US)

(73) Assignee: ARTHREX, INC., Naples, FL (US)

( * ) Notice: Subject to any disclaimer, the term of this patent is extended or adjusted under 35 U.S.C. 154(b) by 836 days.

(21) Appl. No.: 13/756,814

(22) Filed: Feb. 1, 2013

(65) Prior Publication Data

US 2013/0204259 A1 Aug. 8, 2013

Related U.S. Application Data

(60) Provisional application No. 61/595,365, filed on Feb. 6, 2012.

(51) Int. Cl.
*A61B 17/15* (2006.01)
*A61B 17/17* (2006.01)

(52) U.S. Cl.
CPC .......... *A61B 17/154* (2013.01); *A61B 17/155* (2013.01); *A61B 17/1764* (2013.01)

(58) Field of Classification Search
CPC ... A61B 17/154; A61B 17/155; A61B 17/157; A61B 17/1764
USPC .................................... 606/88, 183
See application file for complete search history.

(56) References Cited

U.S. PATENT DOCUMENTS

| | | | |
|---|---|---|---|
| 4,567,886 A * | 2/1986 | Petersen | 606/88 |
| 5,683,397 A | 11/1997 | Vendrely et al. | |
| 5,709,689 A | 1/1998 | Ferrante et al. | |
| 5,810,829 A | 9/1998 | Elliott et al. | |
| 5,860,981 A * | 1/1999 | Bertin et al. | 606/89 |
| 5,976,147 A * | 11/1999 | LaSalle et al. | 606/88 |
| 7,935,150 B2 | 5/2011 | Carignan et al. | |
| 2008/0177261 A1 | 7/2008 | McMin | |
| 2009/0149964 A1 | 6/2009 | May et al. | |

OTHER PUBLICATIONS

Extended European Search Report for Application No. EP 13 15 4188 dated Apr. 16, 2013.

* cited by examiner

*Primary Examiner* — David Bates
*Assistant Examiner* — Olivia C Chang
(74) *Attorney, Agent, or Firm* — Karish & Bjorgum, PC

(57) ABSTRACT

A method for preparing bone to receive a prosthetic implant, according to an exemplary aspect of the present disclosure includes, among other things, positioning a bone preparation guide assembly on a bone, reaming the bone through a first cut opening of the bone preparation guide assembly, dividing the first cut opening into at least two distinct slots and making cuts in the bone through the at least two distinct slots.

18 Claims, 26 Drawing Sheets

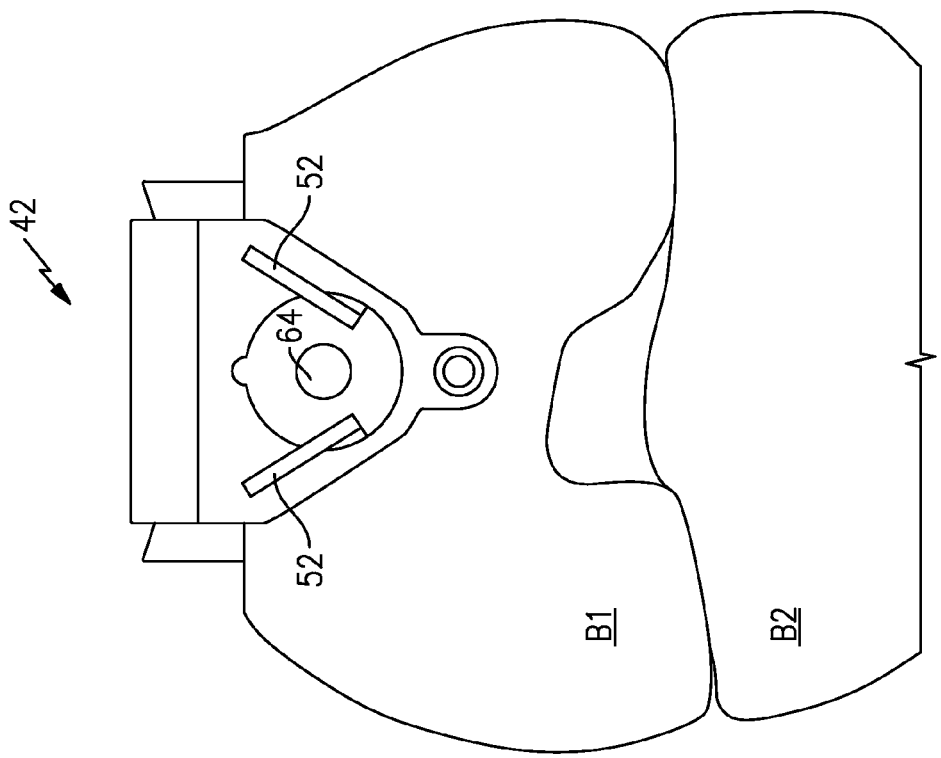
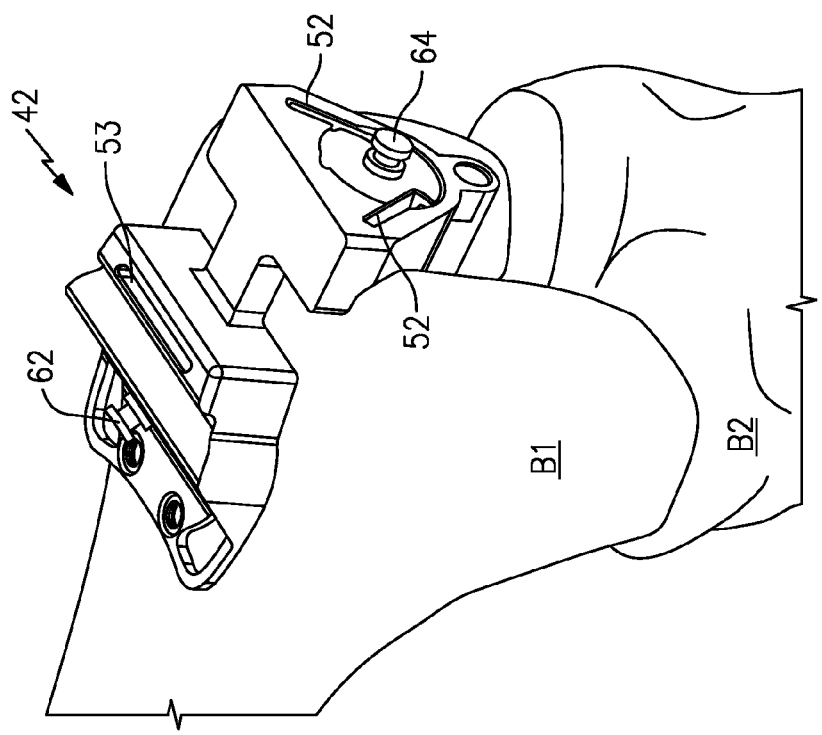

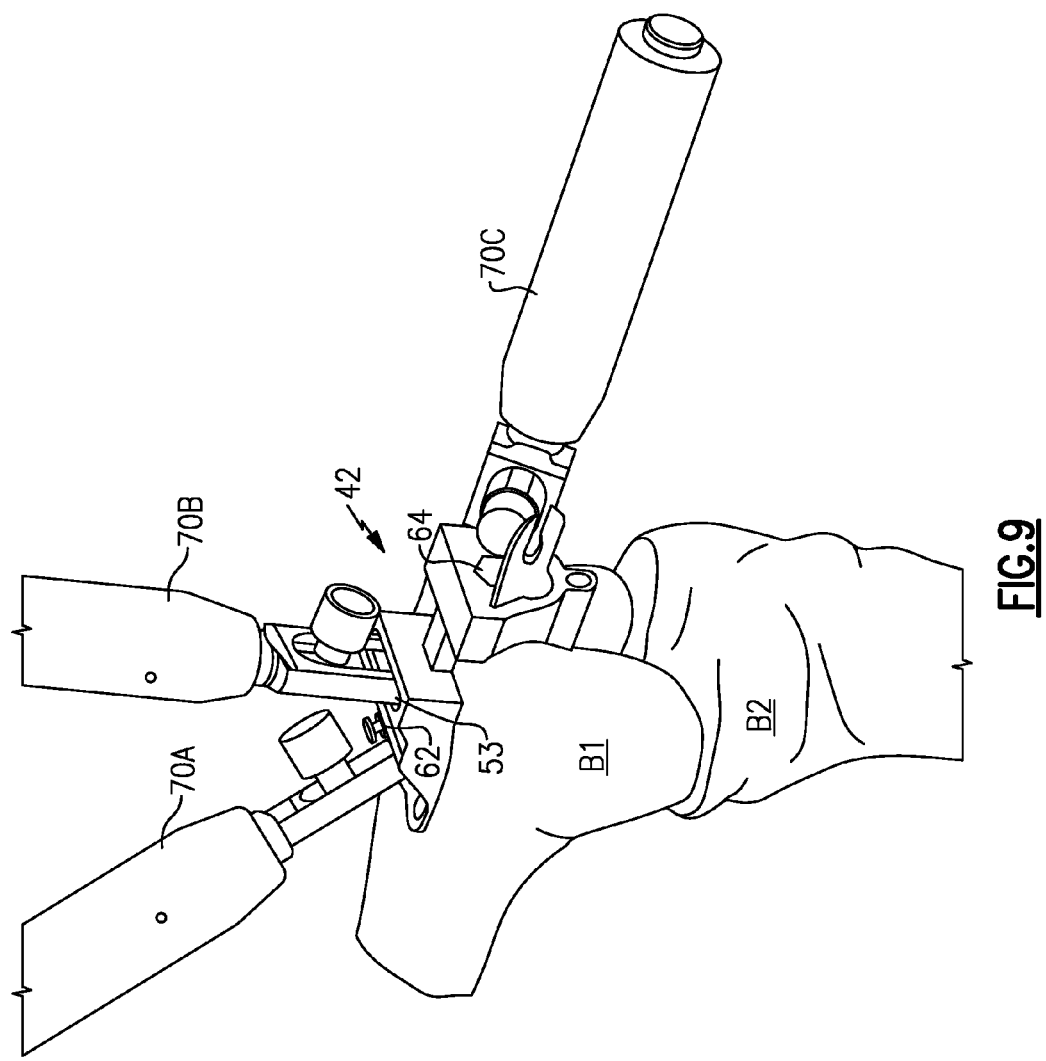

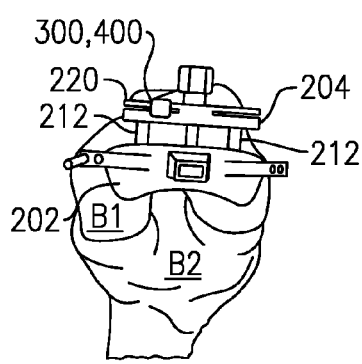
FIG.22B
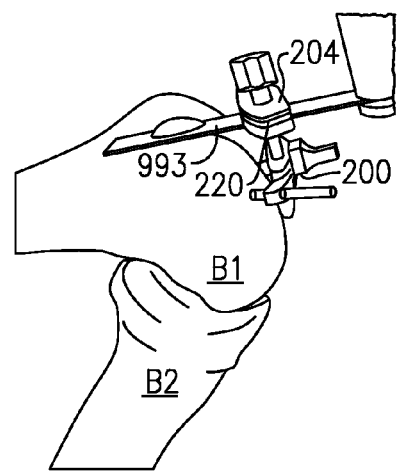
FIG.23A
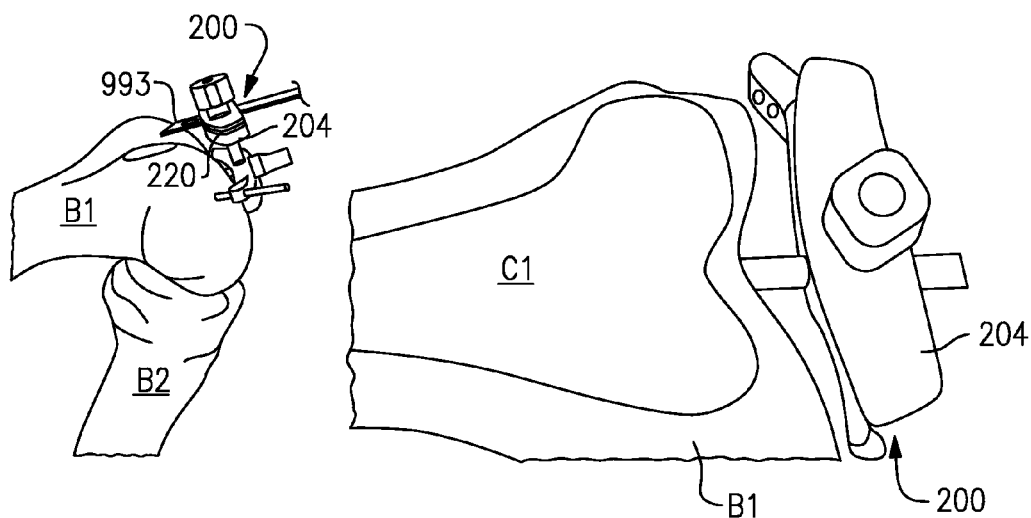
FIG.23B
FIG.23C

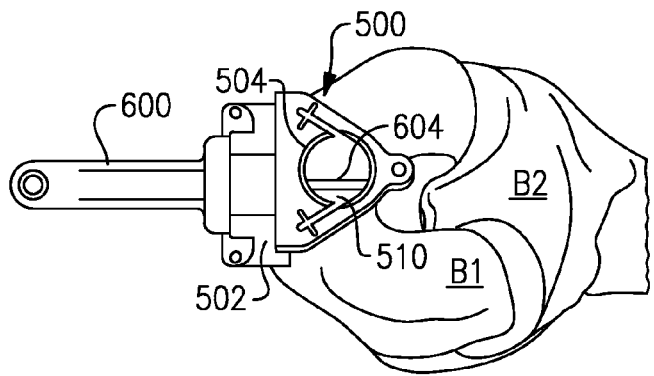
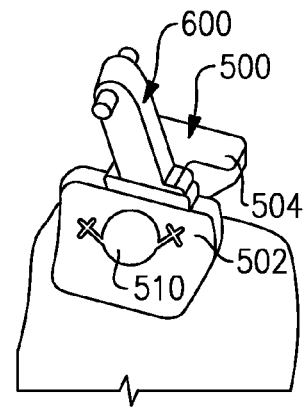
FIG.24A  FIG.24B
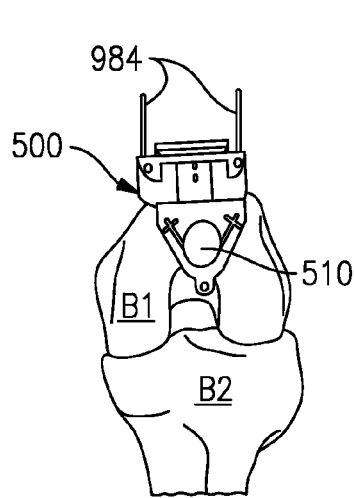
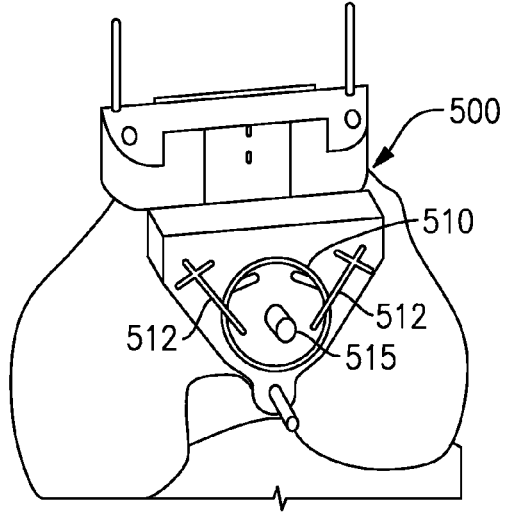
FIG.24C  FIG.25
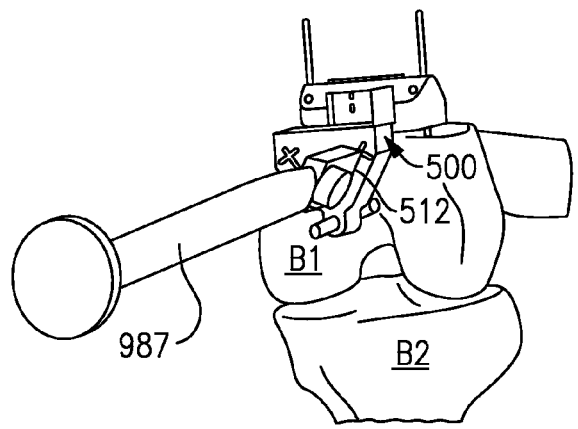
FIG.26

SURGICAL INSTRUMENTATION SET AND SURGICAL TECHNIQUE

CROSS-REFERENCE TO RELATED APPLICATION

This application claims priority to U.S. Provisional Application No. 61/595,365, which was filed Feb. 6, 2012.

BACKGROUND

This disclosure relates to orthopedic surgical instrumentation, and more particularly to a surgical instrumentation set and method of use for preparing bone to receive a prosthetic implant, such as a patello-femoral implant.

Total or partial knee replacement surgery has been performed for many years to treat patients with diseased knee joints. One type of knee replacement surgery that may be required is patello-femoral knee replacement surgery. Patello-femoral knee replacement surgery can be required to address patello-femoral arthritis in the patella-femoral joint that extends between a femur and patella of a knee joint.

Numerous cuts (i.e., resections) must be made in the femur to prepare the femur for receiving a patello-femoral implant. Techniques exist for resecting the femur for this purpose. For example, some techniques require hand sculpting using osteotomes or rasps. However, these techniques are typically performed without the benefit of any guide that can be used to set the position and depth of the various cuts. Other techniques require burring, which may be relatively time consuming and also fail to provide a guide that can be used to establish cut depth and other cut parameters.

SUMMARY

A method for preparing bone to receive a prosthetic implant, according to an exemplary aspect of the present disclosure includes, among other things, positioning a bone preparation guide assembly on a bone, reaming the bone through a first cut opening of the bone preparation guide assembly, dividing the first cut opening into at least two distinct slots and making cuts in the bone through the at least two distinct slots.

In a further non-limiting embodiment of the foregoing method for preparing bone, the at least two distinct slots are smaller than the first cut opening.

In a further non limiting embodiment of either of the foregoing methods for preparing bone, the step of positioning includes aligning a distal proximal stylus within an intercondylar notch of the bone to set a distal-proximal position of the bone preparation guide assembly.

In a further non-limiting embodiment of any of the foregoing methods of preparing bone, the step of aligning includes inserting a post of the distal proximal stylus through an opening in a cut guide of the bone preparation guide assembly.

In a further non-limiting embodiment of any of the foregoing methods of preparing bone, the method includes reaming the bone through a second cut opening of the bone preparation guide assembly, dividing the second cut opening into at least two additional distinct slots and making cuts in the bone through the at least two additional distinct slots of the second cut opening.

In a further non-limiting embodiment of any of the foregoing methods of preparing bone, the steps of making cuts through the at least two distinct slots of the first cut opening and the at least two additional distinct slots of the second cut opening are performed using the same cutting tool.

In a further non-limiting embodiment of any of the foregoing methods of preparing bone, the steps of dividing the first cut opening and the second cut opening include inserting a stabilizer pin into the first cut opening and the second cut opening.

In a further non-limiting embodiment of any of the foregoing methods of preparing bone, the same stabilizer pin is used during the steps of dividing.

In a further non-limiting embodiment of any of the foregoing methods of preparing bone, the step of dividing the first cut opening includes inserting a stabilizer pin into the first cut opening.

In a further non-limiting embodiment of any of the foregoing methods of preparing bone, the method includes the step of making an anterior cut in the bone prior to the step of positioning the bone preparation guide assembly.

In a further non-limiting embodiment of any of the foregoing methods of preparing bone, the step of making the anterior cut in the bone comprises the steps of positioning an anterior cut guide assembly relative to the bone, adjusting a height of the anterior cut guide assembly, and making the anterior cut by inserting a cutting tool through a slot in the anterior cut guide assembly.

In a further non-limiting embodiment of any of the foregoing methods of preparing bone, the method includes the step of placing an implant thickness indicator into the slot of the anterior cut guide assembly prior to the step of adjusting the height.

A surgical instrumentation set, according to an exemplary aspect of the present disclosure includes, among other things, a bone preparation guide assembly that includes a first cut guide having a first cut opening and a stabilizer pin received within the first cut opening to separate the first cut opening into at least two distinct slots.

In a further non-limiting embodiment of the foregoing surgical instrumentation set, a cutting tool is configured to be inserted through the at least two distinct slots.

In a further non-limiting embodiment of either of the foregoing surgical instrumentation sets, the cutting tool is a disposable cutting tool.

In a further non-limiting embodiment of any of the foregoing surgical instrumentation sets, the bone preparation guide assembly includes a second cut guide connected to the first cut guide via a bridge, and the second cut guide includes a second cut opening configured to receive the stabilizer pin to separate the second cut opening into at least two additional distinct slots.

In a further non-limiting embodiment of any of the foregoing surgical instrumentation sets, a slot extends through the first cut guide adjacent to the first cut opening.

In a further non-limiting embodiment of any of the foregoing surgical instrumentation sets, a distal proximal stylus has a post configured to extend through an opening of the slot.

In a further non-limiting embodiment of any of the foregoing surgical instrumentation sets, an anterior cut guide assembly is configured to establish a positioning of the bone preparation guide assembly.

In a further non-limiting embodiment of any of the foregoing surgical instrumentation sets, the bone preparation guide assembly includes a second cut guide that extends generally perpendicular to the first cut guide.

The various features and advantages of this disclosure will become apparent to those skilled in the art from the

BRIEF DESCRIPTION OF THE DRAWINGS

FIGS. 5, 6, 7, 8A, 8B and 9 illustrate a technique for preparing bone to receive a prosthetic implant utilizing the surgical instrumentation set depicted in FIGS. 2-4.

FIGS. 17, 18, 19, 20, 21, 22A, 22B, 23A, 23B, 23C, 24A, 24B, 24C, 25, 26, 27, 28, 29, 30, 31, 32, 33 and 34 illustrate a technique for preparing bone to receive a prosthetic implant utilizing the surgical instrumentation set depicted in FIGS. 11-16.

DETAILED DESCRIPTION

Figure 1:
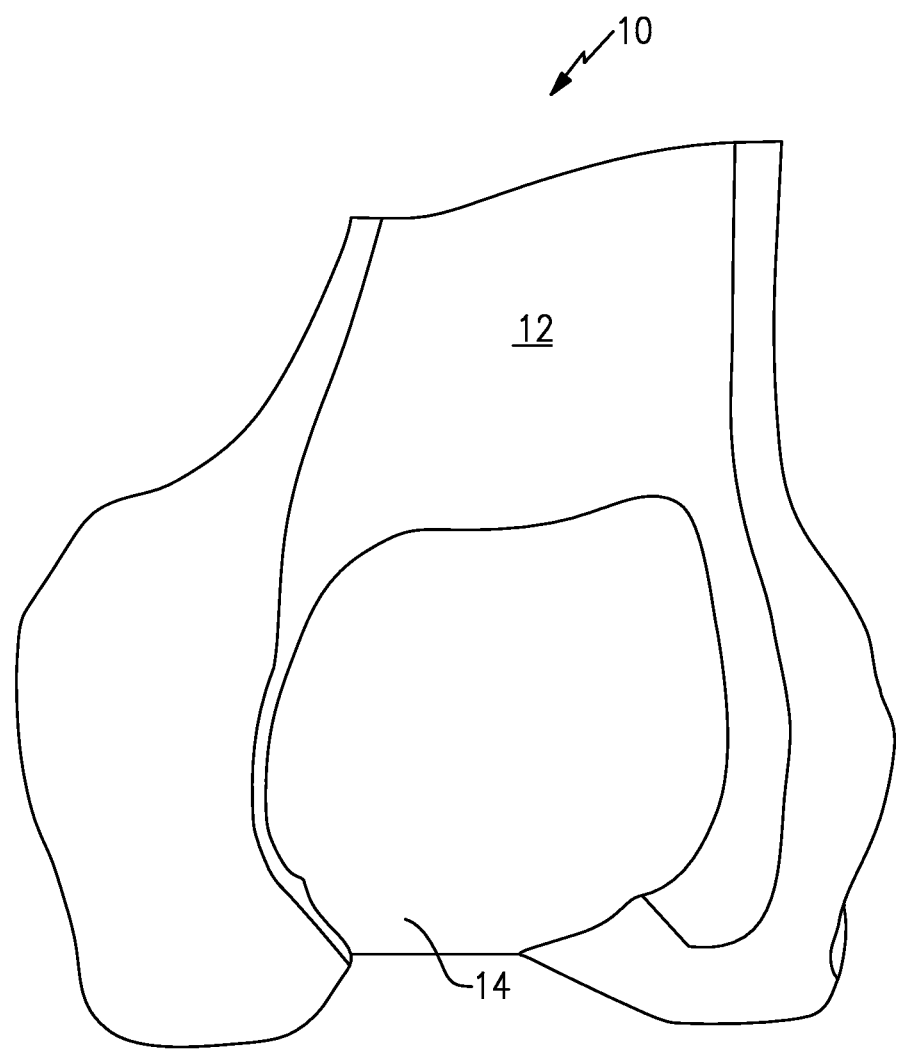
FIG. 1 schematically illustrates a knee joint having a prosthetic implant.

FIG. 1 illustrates a portion of a joint 10, such as a knee joint of the human body. In this embodiment, the joint 10 includes a femur 12, although the joint 10 could include other or additional bones, including but not limited to a tibia and a patella (not shown). Diseased portions of the femur 12 have been removed and replaced with a prosthetic implant 14 that is positionable within the joint 10.

In the exemplary embodiment, the prosthetic implant 14 is a patello-femoral implant. A patello-femoral implant is a prosthetic implant that can be used to repair the patello-femoral joint (space between the patella and a distal portion of the femur 12), such as to address patello-femoral arthritis and/or some other disease. Although the embodiments of this disclosure are presented in the context of implanting a patella-femoral implant, this disclosure could also extend to other implants and to other surgeries.

Figure 2:
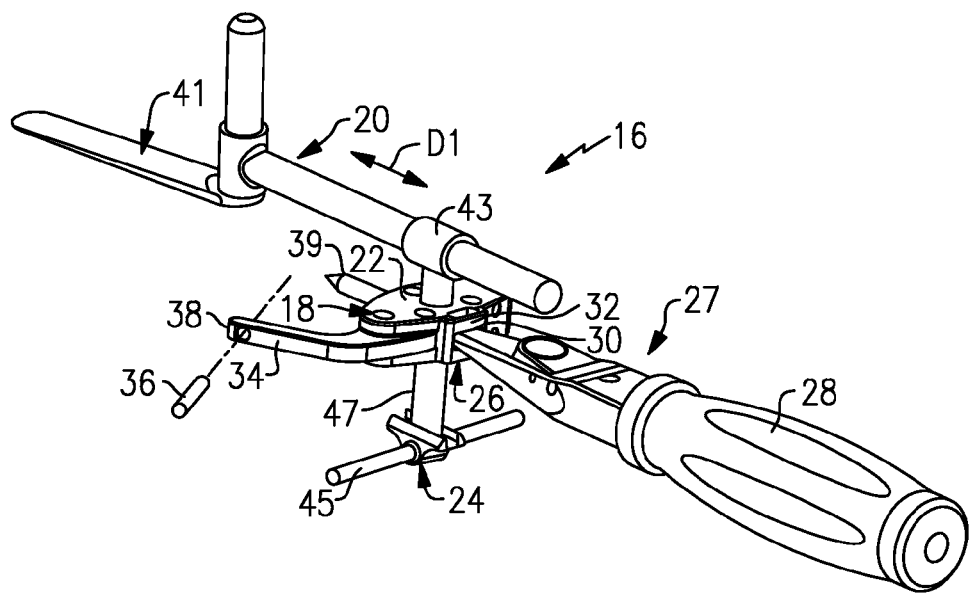
FIG. 2 illustrates an anterior cut guide assembly of a surgical instrumentation set that can be used to resect a bone to prepare the bone for receiving a prosthetic implant.
Figure 3:
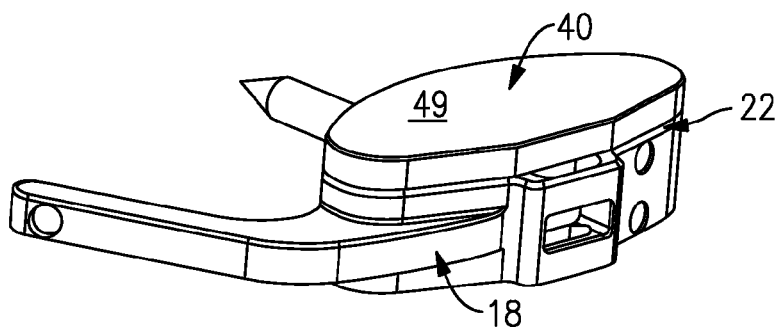
FIG. 3 illustrates an insert that can be used with the anterior cut guide assembly of FIG. 2.

FIGS. 2-4 illustrate various orthopedic surgical instruments that can be used to prepare a bone for the implantation of a prosthetic implant 14 similar to the one illustrated by FIG. 1. In one exemplary embodiment, the orthopedic surgical instruments are part of a surgical instrumentation set that can be used to prepare a patient's femur, such as by sizing, positioning, marking and/or resectioning the femur to receive a patello-femoral implant. It should be understood; however, that the surgical instrumentation set illustrated herein is not limited to uses associated with a patello-femoral implant and could have additional applications related to other prosthetic implants and other surgeries.

Figure 10:
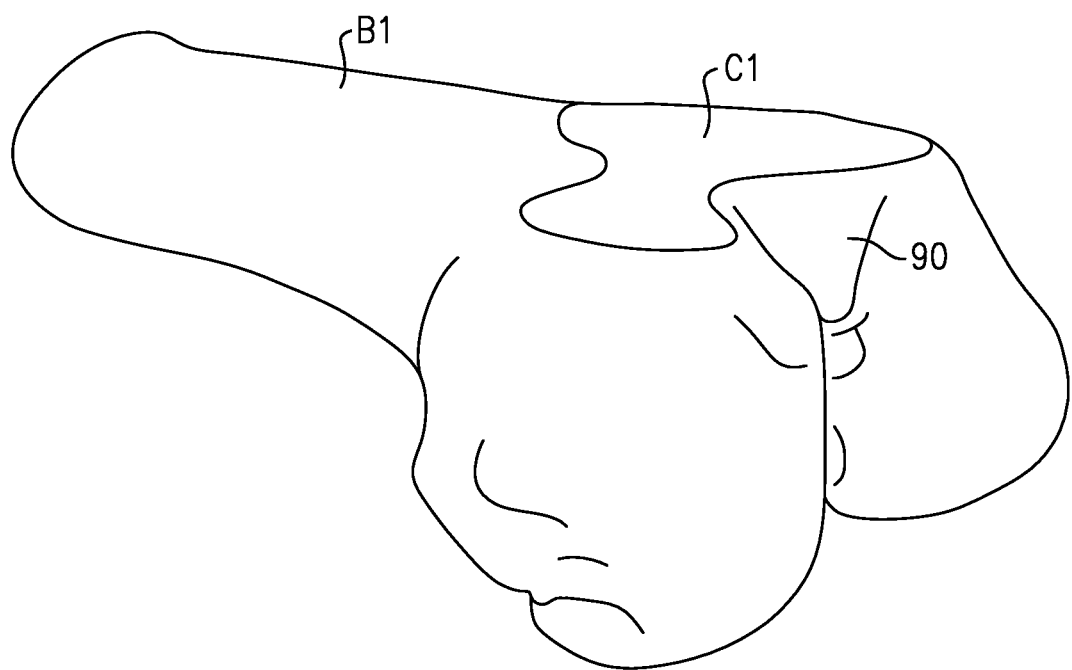
FIG. 10 illustrates a bone that has been resected according to the technique depicted in FIGS. 5-9.

FIG. 2 illustrates an anterior cut guide assembly 16 that can be used to resect bone, such as by making an anterior cut in a femur (see anterior cut C1 in bone B1 of FIG. 10, for example). As discussed in greater detail below, the anterior cut guide assembly 16 can reference an anterior cortex of the femur to control flexion/extension and can reference the posterior condyles of the femur and a longitudinal axis of the tibia to establish internal/external rotation.

In one exemplary embodiment, the anterior cut guide assembly 16 includes a base 18, an anterior cortex reference guide 20 that extends from a top surface 22 of the base 18, a posterior condyle reference guide 24 that extends from a bottom surface 26 of the base 18, and a positioning tool 27 that is selectively engageable relative to a recess 30 of a proximal surface 32 of the base 18. The positioning tool 27 can include a handle 28. The base 18 further includes an arm 34 that can extend about a portion of a bone and is removably securable relative to the bone with a pin 36 or other fastener that can be received through an opening 38 of the arm 34. The base 18 can also include one or more bone spikes 39 (not shown) that can be driven into bone to removably secure the base 18 to the bone.

The anterior cortex reference guide 20 includes a stylus 41 that is moveable in a direction D1 relative to a sleeve 43 that is connected to the base 18. The stylus 41 can be positioned to establish a desired flexion/extension angle of an anterior cut.

The posterior condyle reference guide 24 includes a shaft 45 that is positioned transversely relative to a rod 47 that is connected to the bottom surface 26 of the base 18. The shaft 45 can be pivoted relative to the rod 47 to locate the posterior condyle reference guide 24 at a desired positioning relative to the condyles of the bone.

Additional instrumentation can be used in combination with the anterior cut guide assembly 16 to make an anterior cut in a femur for receiving a prosthetic implant. FIG. 3 illustrates an insert 40 that is selectively engageable relative to the base 18 of the anterior cut guide assembly 16 after removal of the anterior cortex reference guide 20. In the exemplary embodiment, the insert 40 includes a shape that corresponds to the shape of the top surface 22 of the base 18. The insert 40 can be a magnetic insert that magnetically attaches to the top surface 22 of the base 18, although other attachment mechanisms are contemplated. One or more insert(s) 40 can be added to the top surface 22 to establish a desired height (in millimeter increments) of a cutting surface 49 for making an anterior cut into bone. The inserts 40 can be provided in various sizes.

Figure 4A:
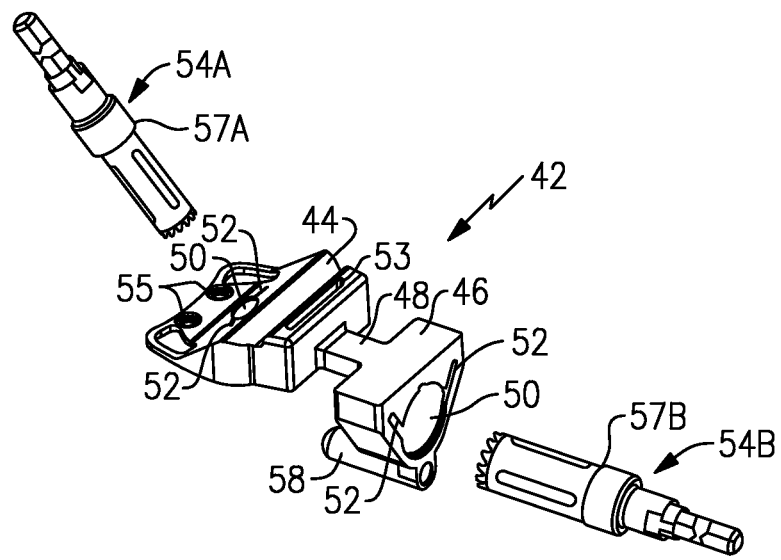
FIGS. 4A, 4B and 4C illustrate a bone preparation guide assembly of a surgical instrumentation set that can be used to prepare various cuts in a bone to prepare the bone for receiving a prosthetic implant.
Figure 4B:
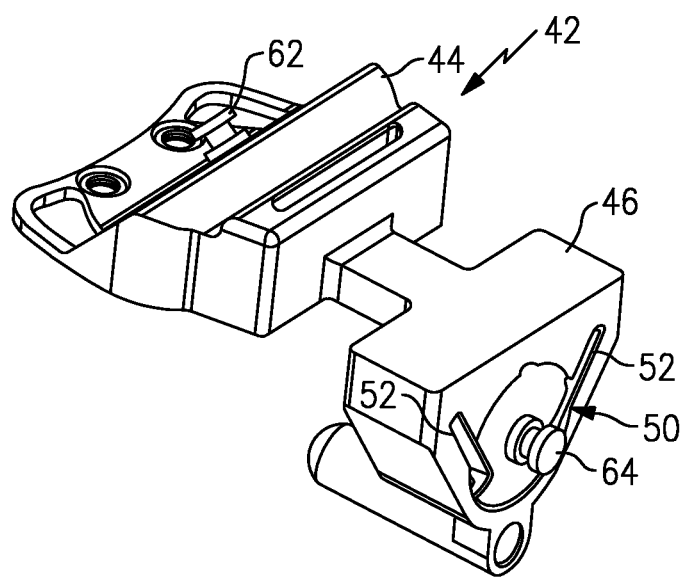
Figure 4C:
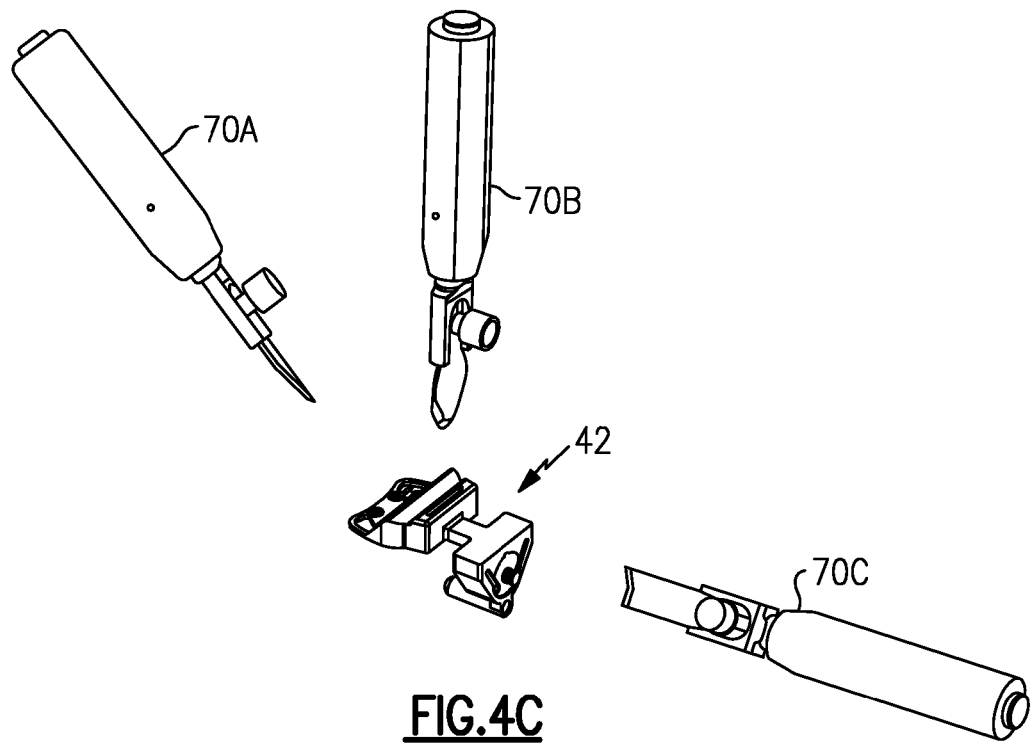

The exemplary surgical instrumentation set can further include a bone preparation guide assembly 42, as is shown in FIGS. 4A, 4B and 4C. The bone preparation guide assembly 42 can be used to further resect bone for implanting a prosthetic implant, such as a patello-femoral implant. The bone preparation guide assembly 42 includes a trochlear cut guide 44 (i.e., a first cut guide) and a distal cut guide 46 (i.e., a second cut guide) connected to the trochlear cut guide 44 via a bridge 48. In the exemplary embodiment, the distal cut guide 46 extends perpendicularly relative to the trochlear cut guide 44. The bone preparation guide assembly 42 can be mounted to bone by inserting fasteners through openings 55 of the trochlear cut guide 44 and into bone.

Each of the trochlear cut guide 44 and the distal cut guide 46 include cut openings 50 that can receive cutting tools 54A, 54B for making trochlear and distal cuts in bone. The cutting tools 54A, 54B could be different cutting tools or the same cutting tool. In the exemplary embodiment, each cutting tool 54A, 54B includes a depth control stop 57A, 57B, respectively, that controls the depth of the cut made through the cut openings 50. The cut openings 50 can also include slots 52 for receiving additional cutting tools (See FIG. 4C, for example).

The trochlear cut guide 44 can also include a slot 53 for making additional cuts in bone, such as with an osteotome or other cutting tool. The distal cut guide 46 may also include a depth pin 58 that establishes a depth of the bone preparation guide assembly 42 relative to an intercondylar notch 60 of a bone B1 (See FIG. 7).

Referring to FIG. 4B, a trochlear stabilizer pin 62 can be inserted into the cut opening 50 of the trochlear cut guide 44 of the bone preparation guide assembly 42 to separate the cut opening 50 into the two distinct slots 52 that are smaller than the cut opening 50. Similarly, a distal stabilizer pin 64 can be inserted into the cut opening 50 of the distal cut guide 46 of the bone preparation guide assembly 42 to separate the cut opening 50 into the two distinct slots 52. The trochlear and distal stabilizer pins 62, 64 establish sizes of the slots 52 and establish a cutting angle of the cutting tools that can be used to make numerous cuts in the bone.

As shown in FIG. 4C, a plurality of cutting tools 70A, 70B and 70C can be used to make various cuts in bone using the bone preparation guide assembly 42, as discussed in greater detail below. In the exemplary embodiment, the cutting tools 70A, 70B and 70C are different osteotomes that can be malleted into bone, although other cutting tools are also contemplated as within the scope of this disclosure.

An example technique for utilizing the surgical instrumentation set illustrated by FIGS. 2-4 to prepare a patient for receiving a prosthetic implant is described below with reference to FIGS. 5-9. In one exemplary embodiment, the surgical instrumentation set is used to resect bone for receiving a patello-femoral implant. The technique described with reference to FIGS. 5-9 is but one exemplary embodiment for utilizing the surgical instrumentation set described above, and it should be understood that fewer or additional steps than recited below could be performed and that the recited order of steps is not intended to limit this disclosure.

Figure 5:
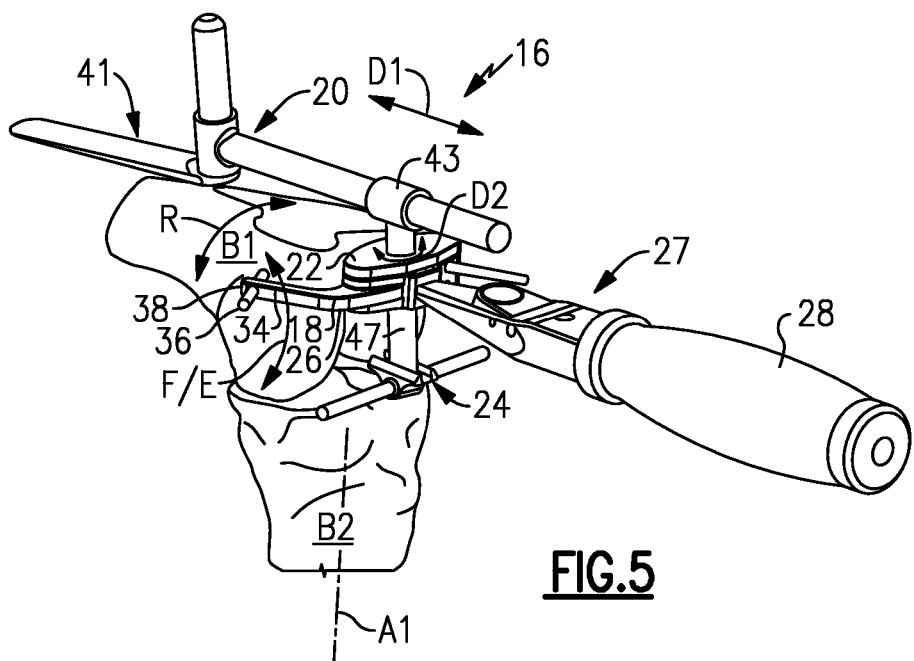

As illustrated by FIG. 5, the technique begins by placing the anterior cut guide assembly 16 relative to a first bone B1 (e.g., a femur) and a second bone B2 (e.g., a tibia) of a patient. In this exemplary embodiment, the anterior cortex reference guide 20 is positioned relative to the first bone B1 and the stylus 41 is moved in the direction D1 (and/or swiveled in the direction D2) to establish a desired flexion/extension angle F/E of an anterior cut C1 (See FIG. 6) of the first bone B1. The flexion/extension angle F/E refers to the angle of the anterior cut C1 with respect to the first bone B1. In one exemplary embodiment, the flexion/extension angle F/E of the anterior cut C1 is set at approximately 5° from an anterior cortex surface of the bone B1, although the actual setting can vary depending on the patient.

Next, the posterior condyle reference guide 24 can be connected to the rod 47 of the sleeve 43 and can be used to set the internal/external rotation R of the anterior cut C1. External rotation refers to tilting the prosthetic implant towards the lateral side of the knee. The posterior condyles are a good rotational guide in a normal healthy knee, therefore, the internal/external rotation R of the anterior cut C1 can be referenced off of the posterior condyles of the first bone B1 and a longitudinal axis A1 of the second bone B2. In one exemplary embodiment, the internal/external rotation of the anterior cut C1 is positioned at approximately 3° from the posterior condyles of the first bone B1.

Once the anterior cortex reference guide 20 and the posterior condyle reference guide 24 are properly positioned, these components are secured to the base 18. The base 18 can then be secured to the first bone B1 by malleting the base 18 such that the bone spike 39 is driven into the first bone B1. Alternatively, the posterior condyle reference guide 24 can be positioned after the base 18 is driven into the first bone B1. A pin 36 can also be malleted through the opening 38 and into the first bone B1 to position the arm 34 and further secure the base 18. The anterior cortex reference guide 20 is connected to the top surface 22 of the base 18 and the posterior condyle reference guide 24 is connected to a bottom surface 26 of the base 18.

The positioning tool 27 can be used to as a guide to align the anterior cut guide assembly 16 relative to the first bone B1 and the second bone B2. For example, the handle 28 of the positioning tool 27 can be used as a reference when viewed from a frontal view and a sagittal view to align a Q-angle and the flexion/extension of the anterior cut guide assembly 16 during set up of the anterior cut guide assembly 16.

Figure 6:
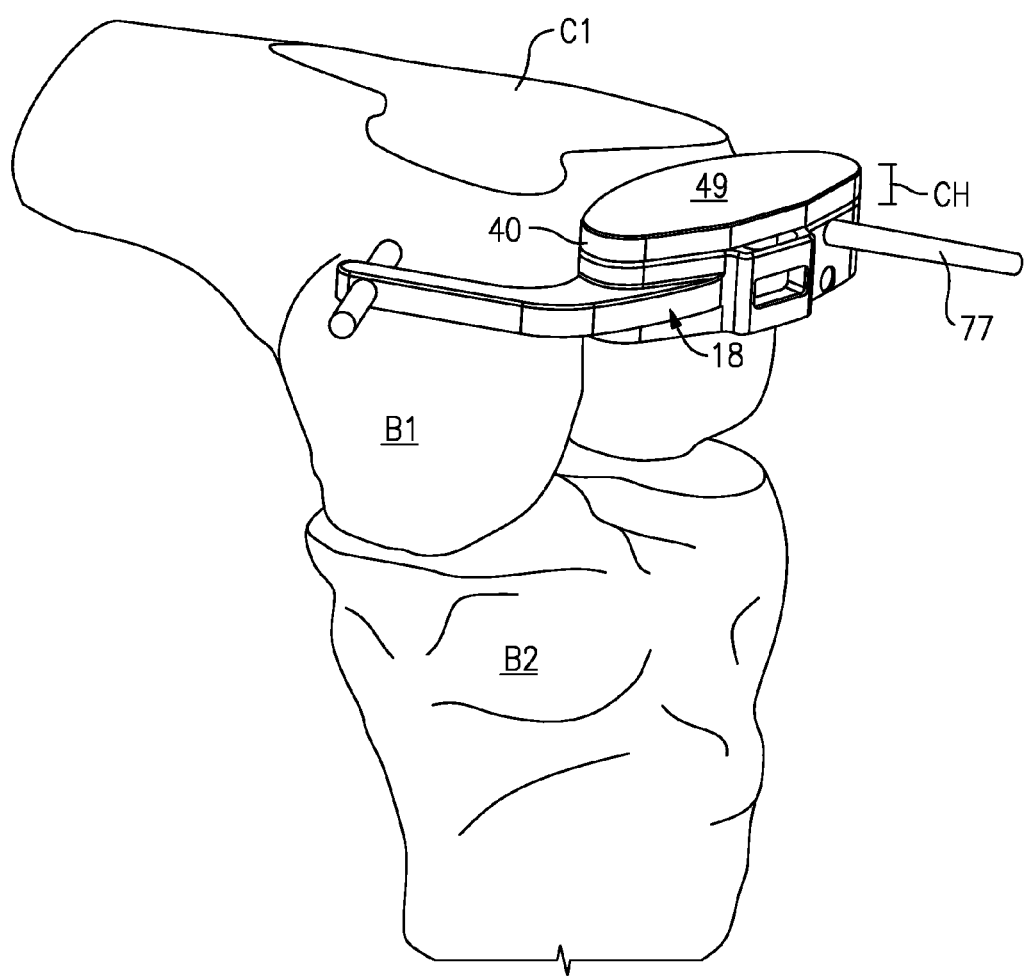

Once the anterior cut guide assembly 16 is appropriately positioned, the anterior cortex reference guide 20 and the posterior condyle reference guide 24 can be removed from the base 18, as shown in FIG. 6. One or more inserts 40 can then be attached to the top surface 22 of the base 18 to establish a desired cut height CH of the anterior cut C1. A surgeon will select the desired cut height CH of the anterior cut C1. A pin 77 can optionally be used to provide additional stability to the base 18 as the anterior cut C1 is made. Once the desired cut height CH is determined and the insert(s) 40 is positioned, a cutting tool (not shown), such as an oscillating saw or other suitable cutting tool, can make the anterior cut C1 in the first bone B1 by using the insert(s) 40 as a guide surface. The base 18 is removed from the bone B1 after the anterior cut C1 is made.

Figure 7:
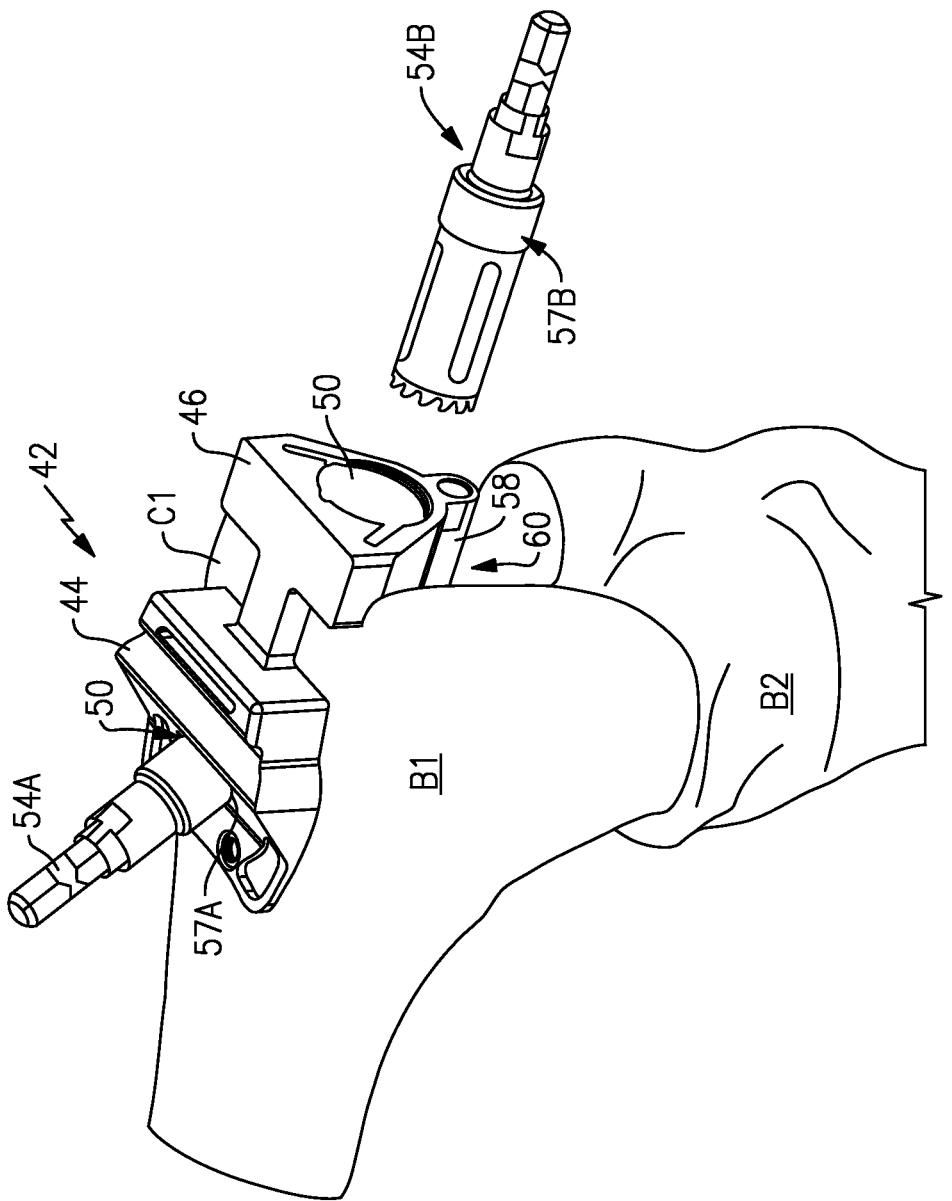

Referring to FIG. 7, the bone preparation guide assembly 42 can be positioned relative to the first bone B1 after the base 18 of the anterior cut guide assembly 16 has been removed. In this exemplary embodiment, the trochlear cut guide 44 of the bone preparation guide assembly 42 is positioned on the anterior cut C1, and the distal cut guide 46 is positioned transversely to the trochlear cut guide 44 by inserting the depth pin 58 into the intercondylar notch 60 of the first bone B1. The surgeon performing the surgery can select the mounting location of the bone preparation guide assembly 42. Once the bone preparation guide assembly 42 is positioned, the cutting tools 54A, 54B (one at a time and in any order) can be inserted through the cut openings 50 to make the trochlear and distal cuts in the first bone B1. The depth control stops 57A, 57B of the cutting tools 54A and 54B can be used to control the depth of the trochlear and distal cuts made through the cut openings 50.

As shown in FIGS. 8A and 8B, the trochlear stabilizer pin 62 can be inserted into the cut opening 50 of the trochlear cut guide 44 and the distal stabilizer pin 64 can be inserted into the cut opening 50 of the distal cut guide 46 after the trochlear and distal cuts have been made in the first bone B1. The trochlear stabilizer pin 62 and the distal stabilizer pin 64 separate each cut opening 50 into a distinct number of slots 52. In this example, the cut openings 50 are divided into two distinct slots 52, although additional slots could be provided. The trochlear stabilizer pin 62 and the distal stabilizer pin 64 also establish the size of each slot 52 and control the cut angle of cuts that are made through the slots 52.

Referring to FIG. 9, various cutting tools 70A, 70B and 70C can be used to make numerous additional cuts in the first bone B1 using the slots 52 established by the trochlear stabilizer pin 62 and the distal stabilizer pin 64 and the slot 53 as cutting guides. In this exemplary embodiment, the cutting tools 70A, 70B and 70C are different sized osteotomes that can be malleted into bone. Other cutting tools are also contemplated as within the scope of this disclosure. Also, in some circumstances, the same cutting tool can be used to make some or all of the cuts. Once these cuts have been made, the bone preparation guide assembly 42 can be removed from the first bone B1 and a prosthetic implant 14 can implanted (See FIG. 1). A trial implant could also be used to confirm that the various cuts are sized appropriately to accept a prosthetic implant.

FIG. 10 illustrates the first bone B1 after various resections have been made using the surgical instrumentation set described above. The surgical instrumentation set can be used to create both the anterior cut C1 and a pocket 90 in the bone B1 for receiving a prosthetic implant 14, such as the patello-femoral implant illustrated by FIG. 1. The pocket 90 is formed by making the trochlear and distal cuts through cut openings 50 and the various other cuts through the slots 52, 53 of the bone preparation guide assembly 42 (See FIGS. 7-9). In one exemplary embodiment, the pocket 90 provides a space for receiving a distal tongue of a prosthetic implant.

FIGS. 11, 12A, 12B, 13, 14, 15A, 15B, 15C, 15D and 16 illustrate another surgical instrumentation set made up of multiple orthopedic surgical instruments that can be used to prepare a bone for the implantation of a prosthetic implant 14 similar to the one illustrated by FIG. 1. In one exemplary embodiment, the surgical instrumentation set can be used to prepare a patient's femur, such as by sizing, positioning, marking and/or resectioning the femur to receive a patello-femoral implant. The surgical instrumentation set may have additional or alternative uses within the scope of this disclosure.

Figure 11:
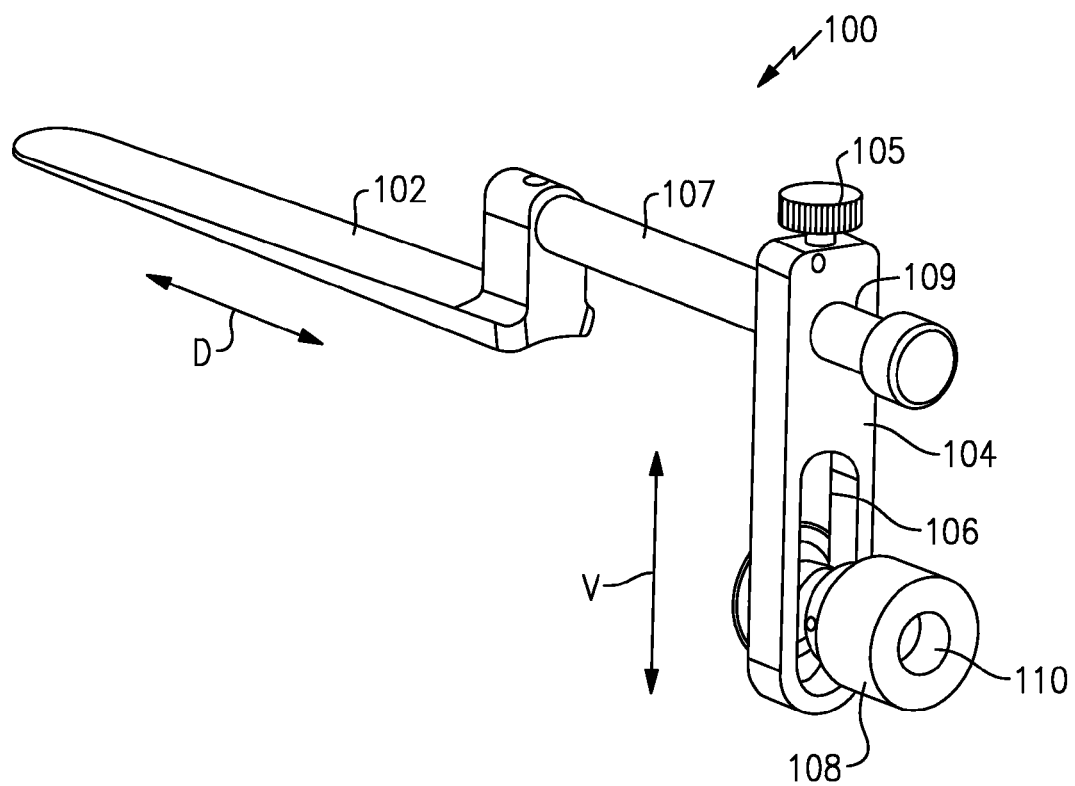
FIG. 11 illustrates an anterior cortex reference guide of a surgical instrumentation set.

FIG. 11 shows an anterior cortex reference guide 100 of the surgical instrumentation set. As discussed in greater detail below, the anterior cortex reference guide 100 can be used to establish a flexion/extension angle of an anterior cut to be made in bone. The anterior cortex reference guide 100 includes a stylus 102 that is moveable in a direction D relative to a guide body 104. The stylus 102 can be positioned to establish a desired flexion/extension angle of an anterior cut. The guide body 104 can include a set screw 105 for locking a positioning of the stylus 102. The set screw 105 can be turned to contact a rod 107 of the stylus 102 that is received within an opening 109 through the guide body 104.

The guide body 104 can also include a slot 106. A knob 108 is vertically adjustable in a direction V within the slot 106. In one embodiment, the knob 108 slides within the slot 106. The knob 108 may include an opening 110 for receiving another surgical instrument, such as a drill, through the knob 108.

Figure 12A:
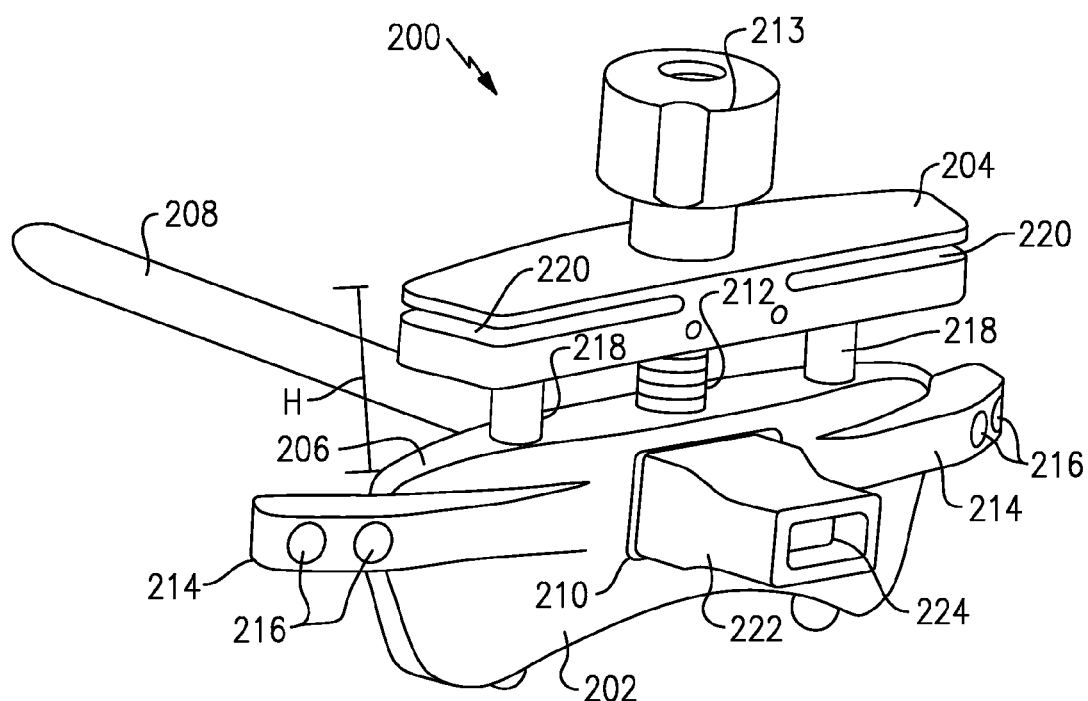
FIGS. 12A and 12B illustrate another exemplary anterior cut guide assembly of a surgical instrumentation set.
Figure 12B:
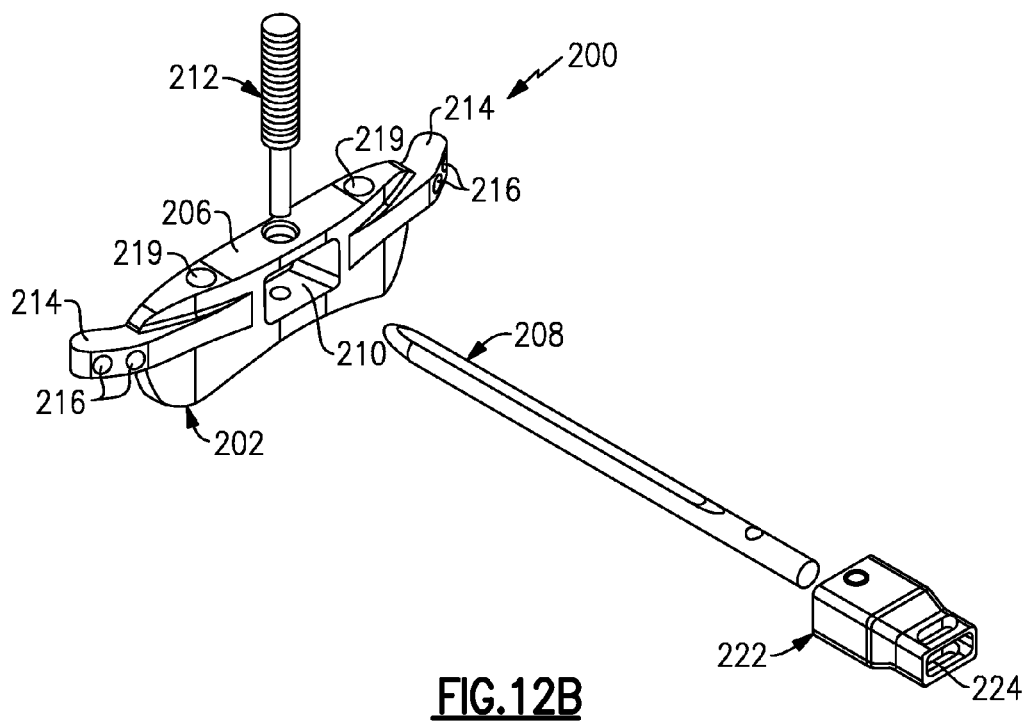

FIGS. 12A and 12B illustrate an anterior cut guide assembly 200 of the exemplary surgical instrumentation set. The anterior cut guide assembly 200 can be used as a guide for establishing an internal/external rotation of an anterior cut and for making the anterior cut in bone. The anterior cut guide assembly 200 of this exemplary embodiment includes a base 202, a cutting block 204 (see FIG. 12A) that extends from a top surface 206 of the base 202, and an intramedullary rod 208 that can be inserted through an opening 210 of the base 202. A post 212 secures the cutting block 204 relative to the base 202.

The base 202 can include a pair of arms 214 that extend from each side of the base 202. The base 202 is removably securable relative to a bone via one or more fasteners (not shown) that can be received through openings 216 formed through the arms 214. The base 202 could alternatively or additionally include one or more bone spikes (not shown) that can be driven into bone to removably secure the base 202 to the bone.

The cutting block 204 includes one or more posts 218 that are received in openings 219 (see FIG. 12B) on the top surface 206 of the base 202. A height H of the cutting block 204 is adjustable relative to the base 202 by adjusting the post 212. The post 212 may include a knob 213 for locking a positioning of the cutting block 204 relative to the base 202. The cutting block 204 includes one or more cutting slots 220 that can receive a cutting tool for making an anterior cut in bone.

In one embodiment, the intramedullary rod 208 is received through the opening 210, which is positioned between the pair of arms 214 of the base 202. A base 222 of the intramedullary rod 208 includes a recess 224 that can accommodate a positioning tool (see FIG. 19) for establishing a desired internal/external rotation of an anterior cut, as discussed in greater detail below.

Figure 13:
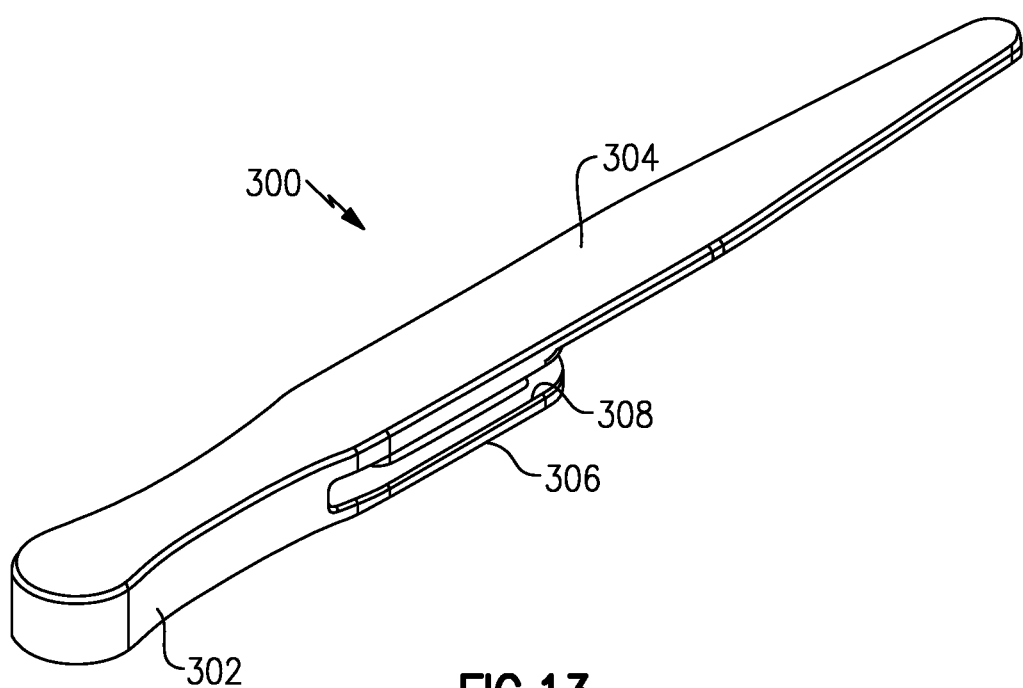
FIG. 13 illustrates an implant thickness indicator.

One embodiment of an implant thickness indicator 300 that can be used in conjunction with the anterior cut guide assembly 200 is shown in FIG. 13. The implant thickness indicator 300 can be used to adjust the height H of the cutting block 204 relative to the base 202. The implant thickness indicator 300 includes a base 302 and an upper prong 304 and a lower prong 306 that extend in the same direction from the base 302. A slot 308 extends between the upper prong 304 and the lower prong 306. In one embodiment, the upper prong 304 has a greater length than the lower prong 306. The lower prong 306 may be received within the cutting slots 220 of the cutting block 204. The upper prong 304 may rest on a portion of bone as a reference point for establishing a desired height of the cutting block 204.

Figure 14:
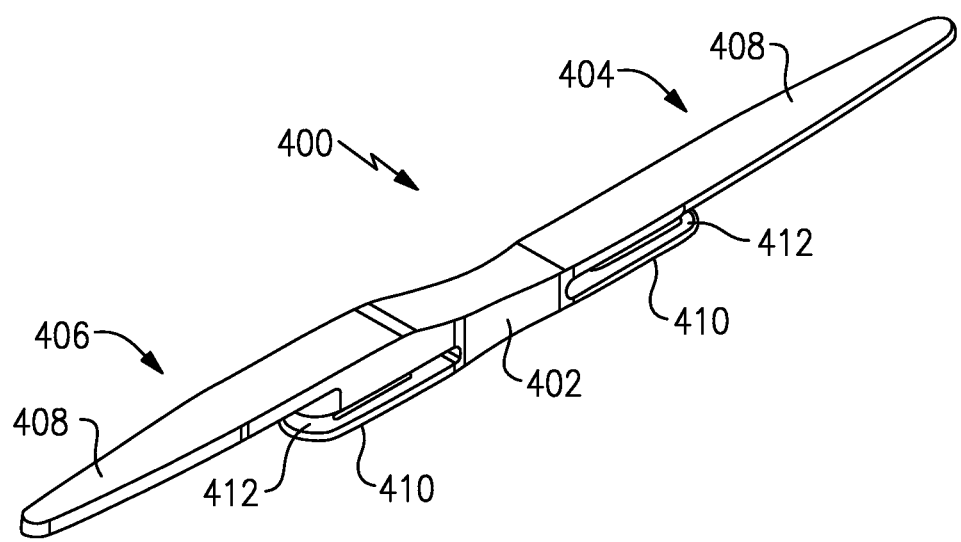
FIG. 14 illustrates another implant thickness indicator embodiment.

Another implant thickness indicator 400 that can alternatively be used in conjunction with the anterior cut guide assembly 200 to adjust the height H of the cutting block 204 is illustrated in FIG. 14. The implant thickness indicator 400 is a two-sided indicator that includes a base 402 and a first prong 404 and a second prong 406 that extend in opposite directions from the base 402. Each of the first prong 404 and the second prong 406 includes an upper prong 408, a lower prong 410 and a slot 412 that extends between the upper prong 408 and the lower prong 410. In one embodiment, the upper prongs 408 are greater in length than the lower prongs 410. The lower prongs 410 may be received within the cutting slots 220 of the cutting block 204. In this embodiment, the first prong 404 can be used to adjust a desired height of the cutting block 204 and the second prong 406 can be used to reference the condyle height of an implant and provide a secondary check to ensure that additional height/material are not being resected when preparing for the receipt of the implant.

Figure 15A:
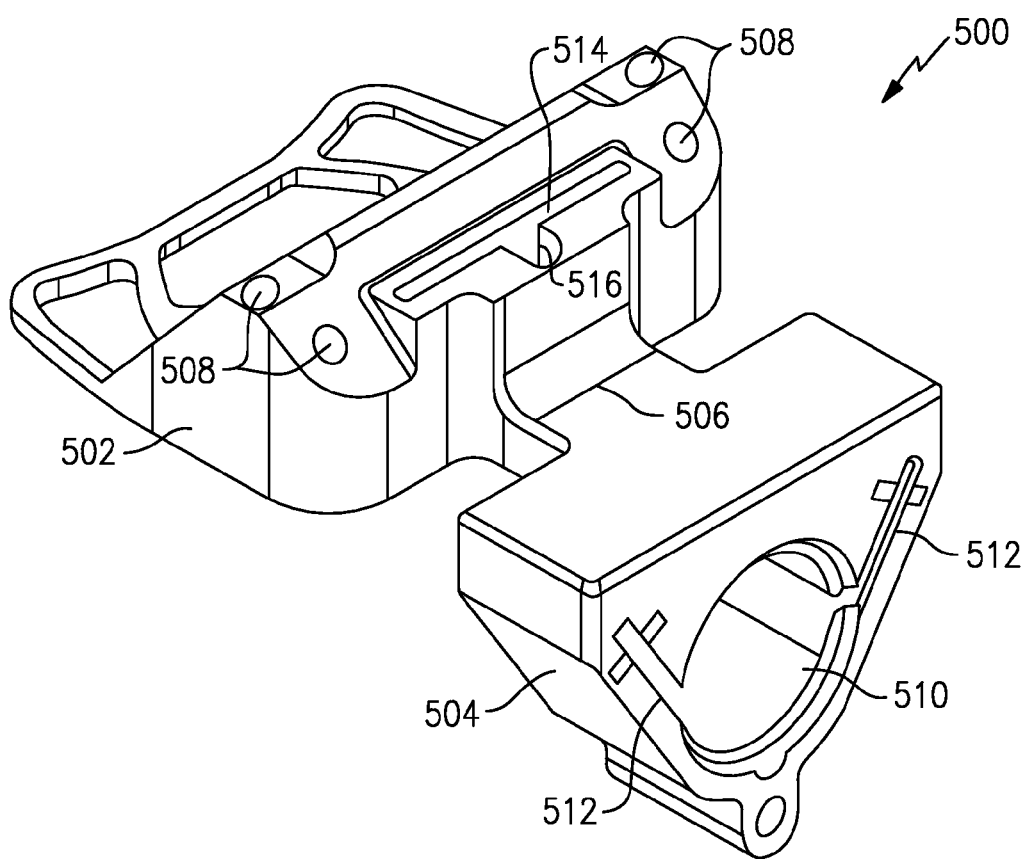
FIGS. 15A and 15B illustrate another bone preparation guide assembly of a surgical instrumentation set.
Figure 15B:
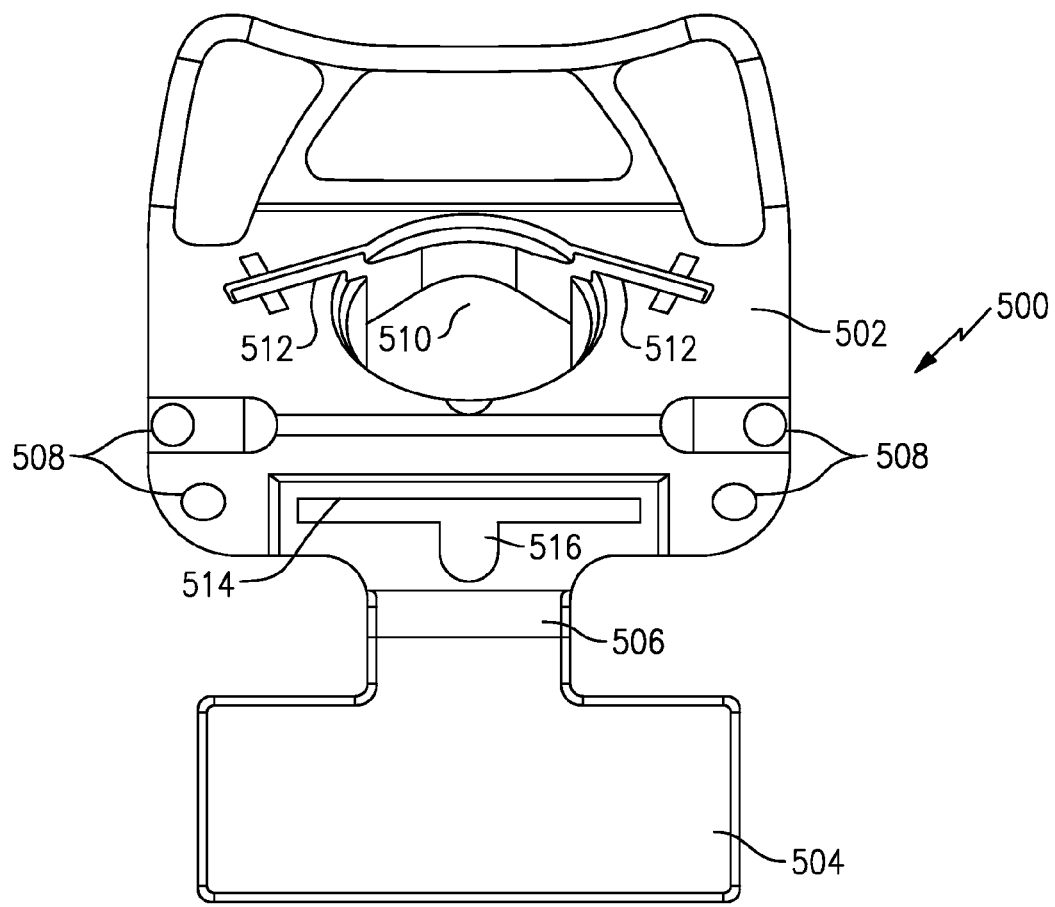

Referring to FIGS. 15A and 15B, a bone preparation guide assembly 500 of the surgical instrumentation set can be used to further resect bone for implanting a prosthetic implant. The bone preparation guide assembly 500 can include a proximal cut guide 502 (i.e., a first cut guide) and a distal cut guide 504 (i.e., a second cut guide) connected to the proximal cut guide 502 via a bridge 506. In the exemplary embodiment, the distal cut guide 504 extends perpendicularly relative to the proximal cut guide 502. The bone preparation guide assembly 500 can be mounted to bone by inserting fasteners, such as pins, through openings 508 of the proximal cut guide 502 and into bone.

Figure 15C:
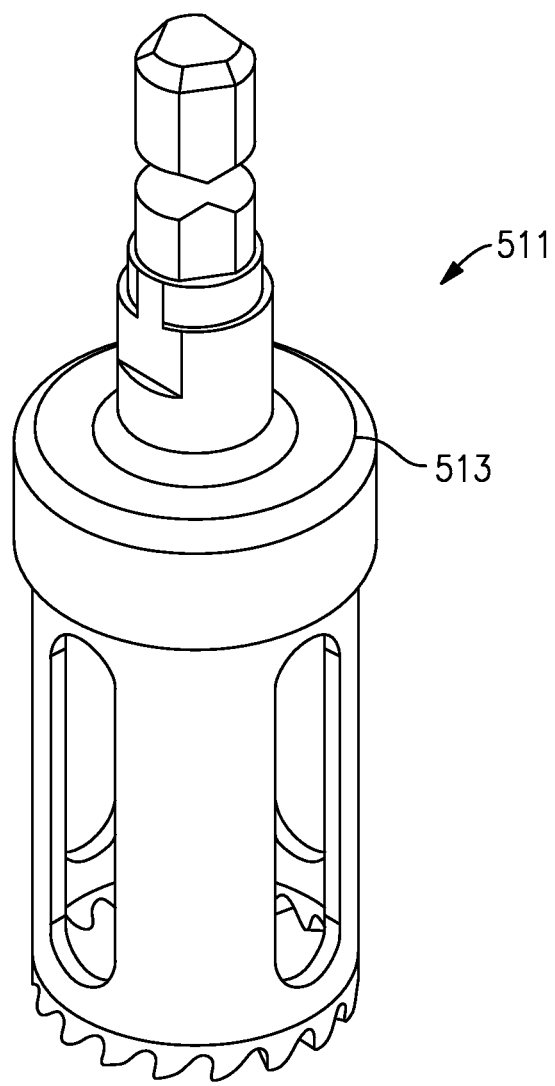
FIG. 15C illustrates a cutting tool.

Each of the proximal cut guide 502 and the distal cut guide 504 include cut openings 510 that can receive a cutting tool 511 (see FIG. 15C) for making trochlear and distal cuts in bone. The same cutting tool 511 is used to make cuts through the cut openings 510, in this embodiment. As shown in FIG. 15C, the cutting tool 511 can include a depth control stop 513 that controls the depth of the cut made through the cut openings 510. The cut openings 510 of the proximal cut guide 502 and the distal cut guide 504 can also include slots 512 for receiving additional cutting tools.

The proximal cut guide 502 can also include a slot 514 for making additional cuts in bone, such as with an osteotome or other cutting tool. The slot 514 extends through the proximal cut guide 502 at a position offset from the cut opening 510 (in a direction toward the bridge 506). The slot 514 may include an opening 516 for accommodating yet another tool, such as a distal proximal stylus, as discussed in greater detail below. In one embodiment, the slot 514 and the opening 516 form a T-shape.

Figure 15D:
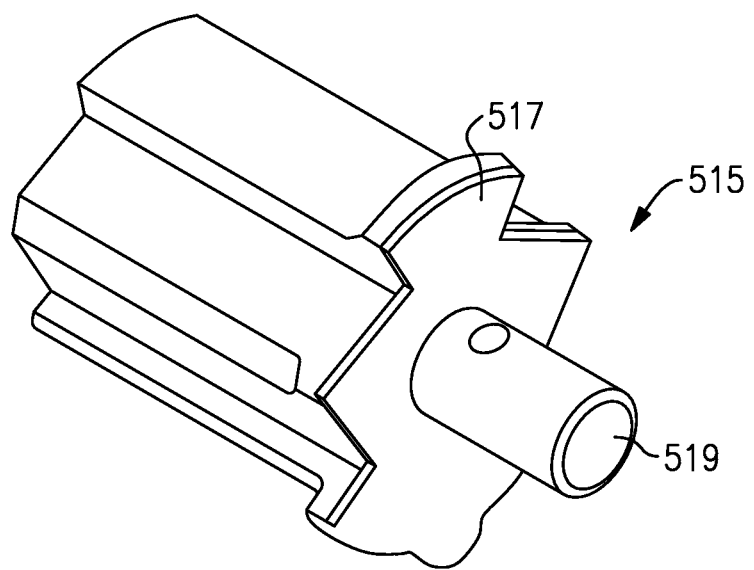
FIG. 15D illustrates a stabilizer pin.

Referring to FIG. 15D, a stabilizer pin 515 can be inserted into the cut opening 510 of the proximal cut guide 502 of the bone preparation guide assembly 500 to separate the cut opening 510 into the two distinct slots 512 that are smaller than the cut openings 510. Similarly, the stabilizer pin 515 can be inserted into the cut opening 510 of the distal cut guide 504 of the bone preparation guide assembly 500 to separate the cut opening 50 into at least two additional distinct slots 512.

The stabilizer pin 515 may include a plug portion 517 that is received within the cut openings 510 and a post portion 519 that protrudes out of the cut openings 510. The stabilizer pin 515 establishes the sizes of the slots 512 and establishes a cutting angle of the cutting tools that can be used to make numerous cuts in the bone, such as for preparing a pocket in the bone.

Figure 16:
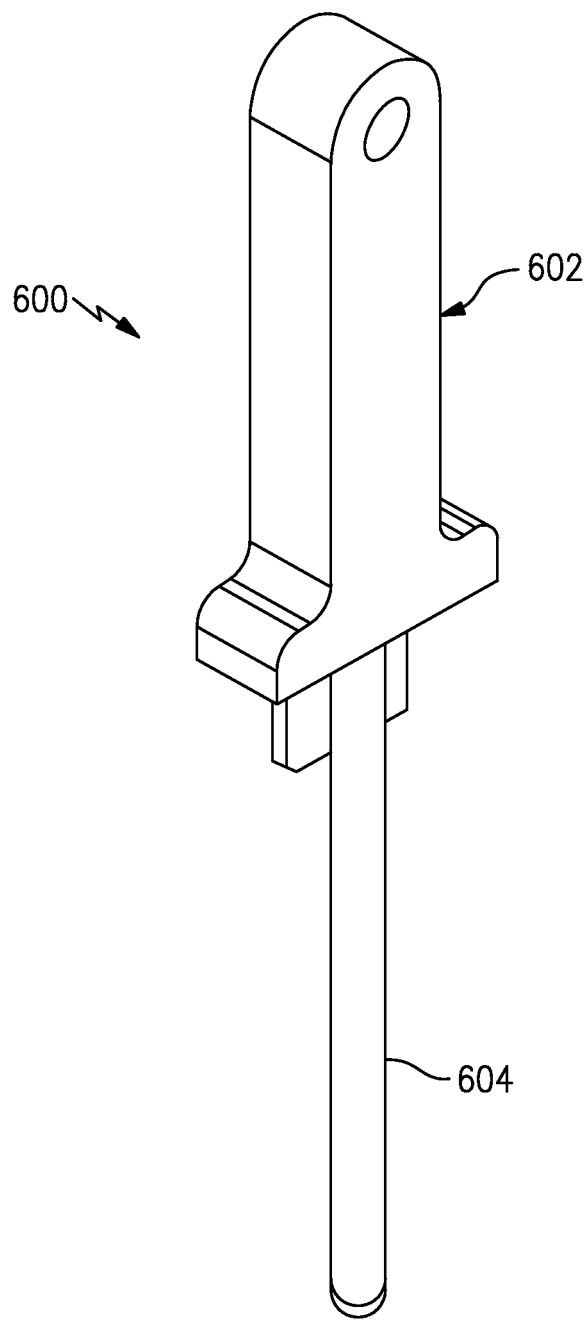
FIG. 16 illustrates a distal proximal stylus.

FIG. 16 illustrates a distal proximal stylus 600 that can be used with the bone preparation guide assembly 500 to set a position of an implant in the proximal distal direction. The distal proximal stylus 600 includes a handle 602 and a post 604 that extends from the handle 602. The post 604 of the distal proximal stylus 600 may be received through the opening 516 of the proximal cut guide 502 of the bone preparation guide assembly 500 to align the distal proximal stylus 600 within an intercondylar notch of the bone, as is discussed in more detail below.

An example technique for utilizing the surgical instrumentation set illustrated in FIGS. 11 through 16 to prepare a patient for receiving a prosthetic implant is described below with reference to FIGS. 17 through 34. In one exemplary embodiment, the surgical instrumentation set is used to resect bone for receiving a patello-femoral implant. The technique described with reference to FIGS. 17 through 34 is but one exemplary embodiment for utilizing the surgical instrumentation set described above, and it should be understood that fewer or additional steps than recited below could be performed and that the recited order of steps is not intended to limit this disclosure.

Figure 17:
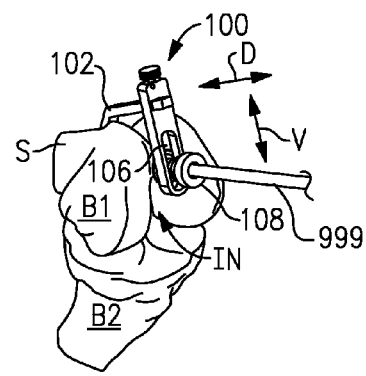

As illustrated by FIG. 17, the technique begins by positioning the anterior cortex reference guide 100 relative to a first bone B1 (e.g., a femur) and a second bone B2 (e.g., a tibia) of a patient. In this exemplary embodiment, the stylus 102 of the anterior cortex reference guide 100 is placed along a shaft S of the first bone B1 and can be moved in the direction D to establish a desired flexion/extension angle of an anterior cut that is to be made in the first bone B1. The flexion/extension angle refers to the angle of the anterior cut C1 (see FIG. 23C) with respect to the first bone B1. In one exemplary embodiment, the flexion/extension angle of the anterior cut is set at approximately 5° from an anterior cortex surface of the first bone B1, although the actual setting can vary depending on the patient.

The positioning of the knob 108 of the anterior cortex reference guide 100 can also be adjusted in the direction V within the slot 106. In one embodiment, the knob 108 is adjusted to be approximately 1 cm above the bottom of the intercondylar notch IN of the first bone B1. Other positions are also contemplated and may vary from patient to patient and surgery to surgery.

Figure 18:
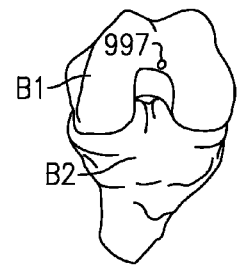

Once the positioning of the anterior cortex reference guide 100 is achieved, a tool 999, such as a drill, can be inserted through the opening 110 of the knob 108 to drill a hole 997 into the bone B1 (see FIG. 18). The anterior cortex reference guide 100 may be removed from the bone B1 after preparing the hole 997.

Figure 19:
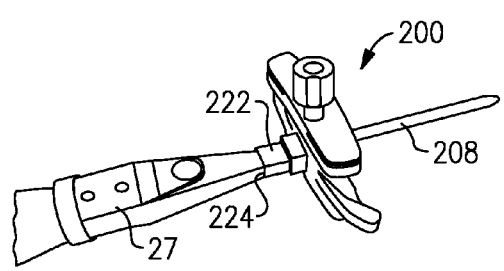
Figure 20:
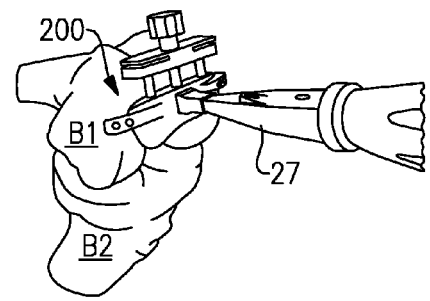

Referring to FIGS. 19 and 20, the technique may continue by inserting a positioning tool 27 into the recess 224 of the base 222 of the intramedullary rod 208 of the anterior cut guide assembly 200. The intramedullary rod 208 can then be inserted through the hole 997 (see FIG. 18) previously formed in the first bone B1 to position the anterior cut guide assembly 200 relative to the first bone B1. The anterior cut guide assembly 200 is then adjusted to establish an internal/external rotation of an anterior cut. In one embodiment, the internal/external rotation is set at approximately 3 degrees from the posterior condyles of the first bone B1.

Figure 21:
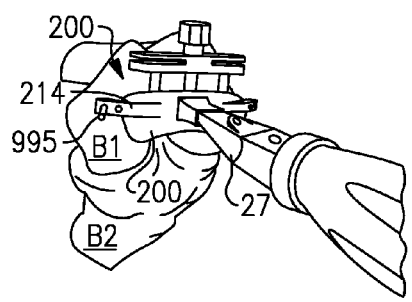

Once properly positioned, the anterior cut guide assembly 200 is secured to the first bone B1. As shown in FIG. 21, one or more fasteners 995 may be inserted through the openings 216 of the arms 214 of the base 202 to secure the anterior cut guide assembly 200.

Figure 22A:
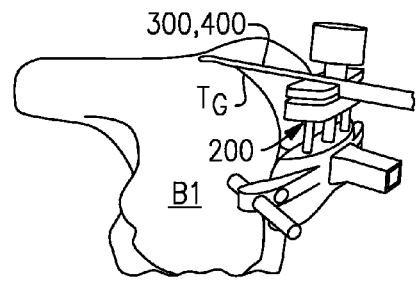

Next, as shown in FIGS. 22A and 22B, the implant thickness indicator 300 (or alternatively the implant thickness indicator 400) can be inserted into one of the cutting slots 220 of the cutting block 204 to adjust the height of the cutting block 204. This step ensures that the anterior cut thickness matches a thickness of the implant. In one embodiment, the height of the cutting block 204 is adjusted (e.g., by adjusting the height of the posts 212) until the implant thickness indicator 300, 400 touches a low point of the trochlear groove TG of the first bone B1 (best illustrated in FIG. 22B).

The implant thickness indicator 300, 400 can be removed once a desired positioning is achieved. FIGS. 23A, 23B and 23C illustrate the insertion of a cutting tool 993 through the cutting slots 220 of the cutting block 204 to prepare the anterior cut C1 in the first bone B1. The anterior cut guide assembly 200 can be removed once the anterior cut C1 has been made.

Next, the bone preparation guide assembly 500 may be positioned on the first bone B1 (see FIG. 24A). The cut openings 510 may be aligned within the surface of the anterior cut C1 made in the prior steps. The distal proximal stylus 600 can next be used to set a position of an implant in the proximal distal direction. For example, the post 604 of the distal proximal stylus 600 may be inserted through the opening 516 of the proximal cut guide 502 of the bone preparation guide assembly 500 (see FIG. 16 and FIGS. 24A and 24B) to align the distal proximal stylus 600 within an intercondylar notch of the first bone B1. Once a desired positioning is achieved, the bone preparation guide assembly 500 can be pinned to the first bone B1 using fasteners 989 (see FIG. 24C). Next, a cutting tool, such as the cutting tool 511 shown by FIG. 15C, can be used to ream the first bone B1 through each of the cut openings 510 (not shown).

As shown in FIGS. 25 and 26, the stabilizer pin 515 may be inserted into the cut opening 510 of the distal cut guide 504 to divide the cut opening 510 into at least two distinct slots 512. A cutting tool 987 (see FIG. 26) can be inserted through the at least two distinct slots 512 to make additional cuts in the first bone B1. In one embodiment, the cutting tool 987 is a disposable tool.

Figure 27:
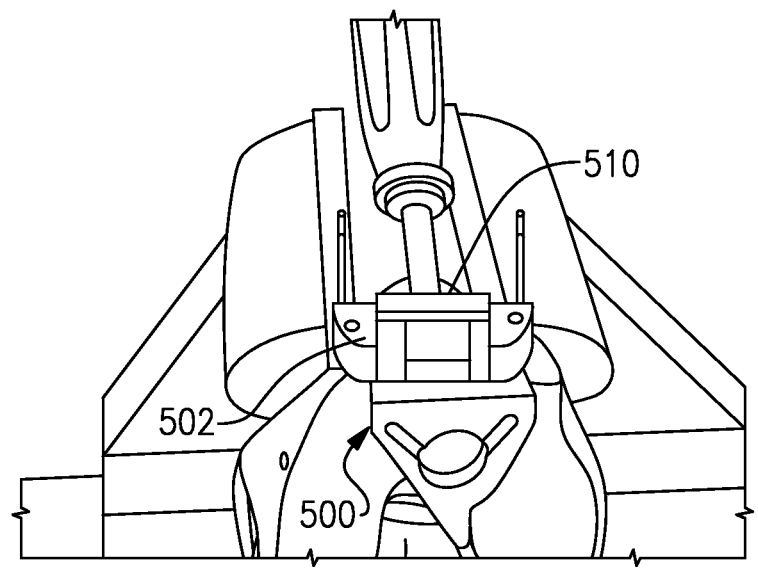
Figure 28:
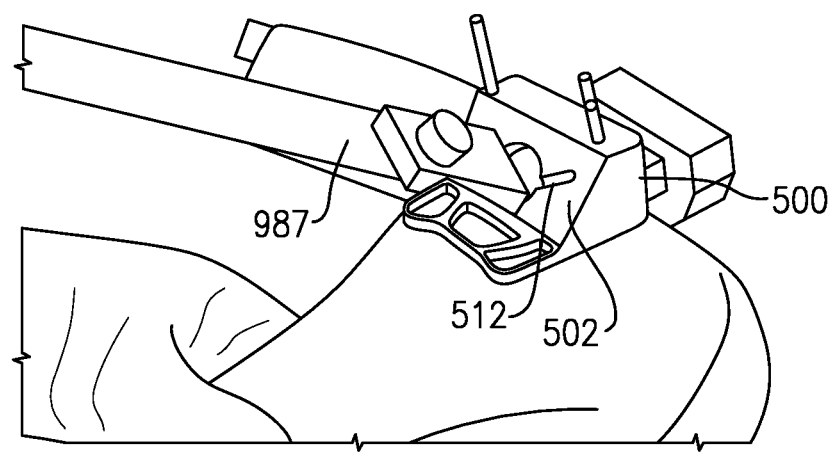
Figure 29:
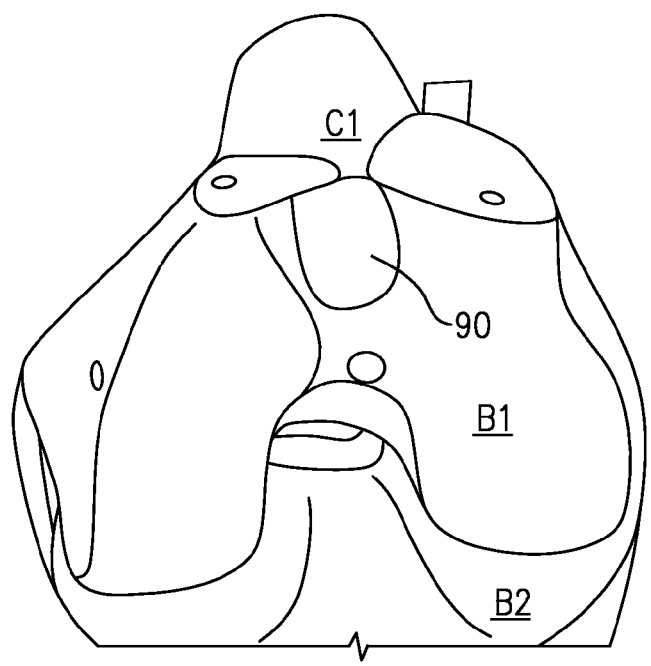

Subsequently, the stabilizer pin 515 can be removed from the distal cut guide 504 and can be inserted into the cut opening 510 of the proximal cut guide 502. Alternatively, the cuts can be made through the slots 512 of the proximal cut guide 502 first. In other words, the order of these cuts is not intended to be limiting. The same cutting tool 987 can be inserted through the at least two additional distinct slots 512 of the proximal cut guide 502 to make additional cuts in the first bone B1. These steps are schematically illustrated in FIGS. 27 and 28. Once all cuts are made, the bone preparation guide assembly 500 may be removed from the first bone B1, leaving a prepared pocket 90 for placement of an implant (see FIG. 29).

Figure 30:
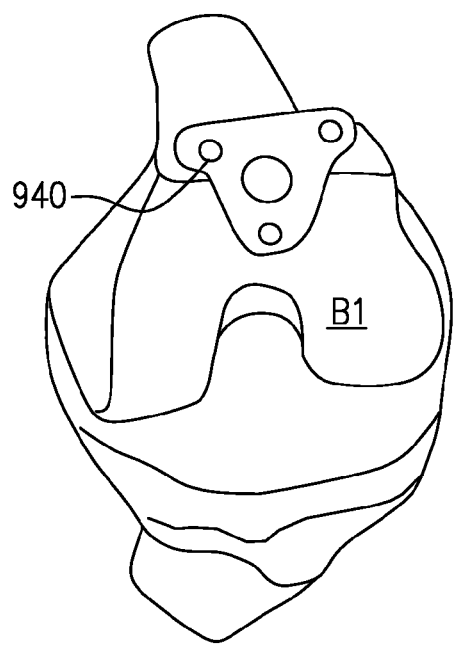
Figure 31:
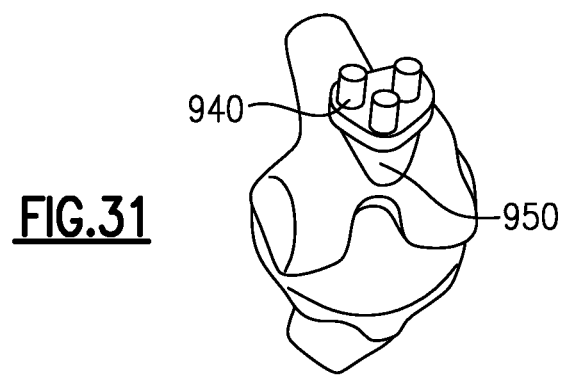
Figure 32:
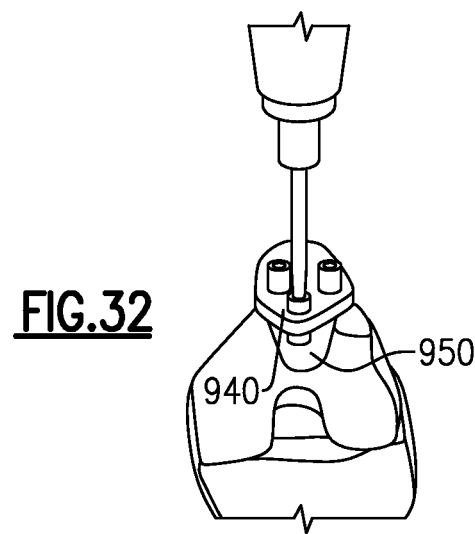
Figure 33:
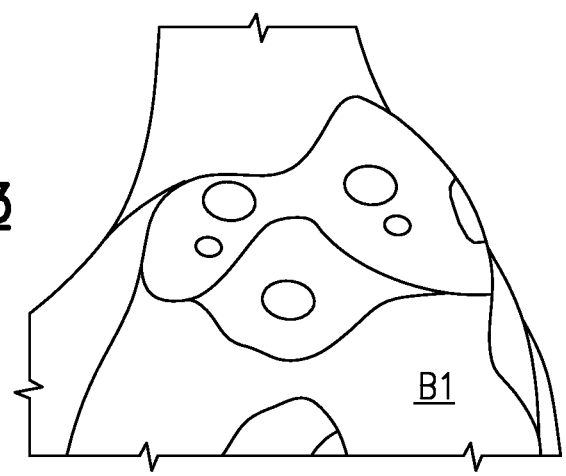
Figure 34:
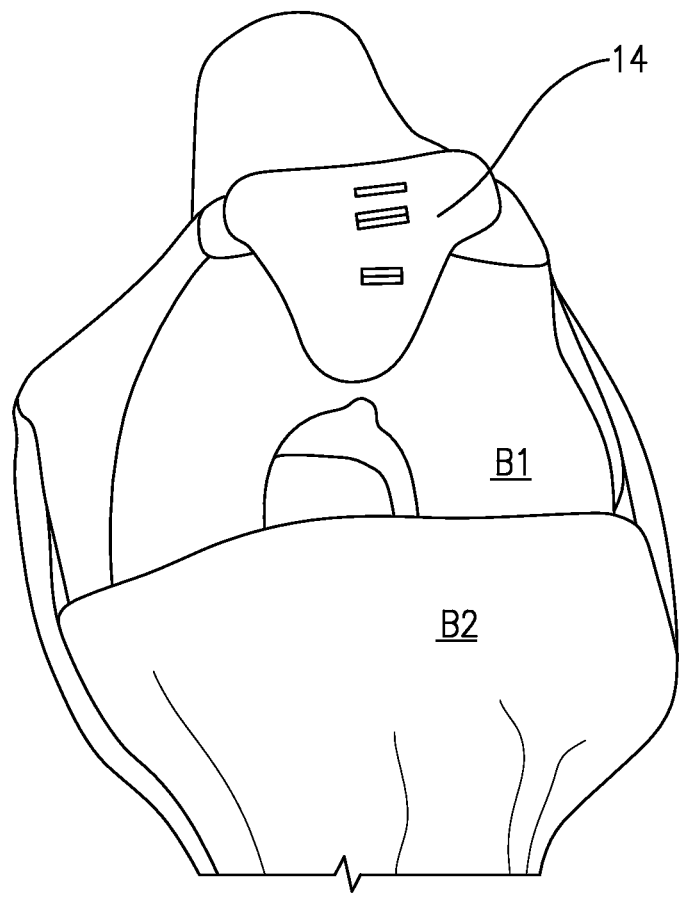

FIGS. 30, 31, 32 and 33 illustrate additional steps that can be performed to prepare the first bone B1 for receiving an implant. As shown in FIG. 30, a trial implant 950 can be positioned on the prepared surfaces of the first bone B1. Next, as shown in FIG. 31, a peg drill stabilizer 940 can be positioned over the trial implant 950. Holes are then drilled into the first bone B1 through openings in the peg drill stabilizer 940 (see FIG. 32). The peg drill stabilizer 940 and the trial implant 950 can then be removed (see FIG. 33). Finally, as shown in FIG. 34, a prosthetic implant 14 can be inserted into the prepared openings of the first bone B1.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical instrumentation set, comprising:
a bone preparation guide assembly that includes a first cut guide having a first cut opening;
a stabilizer pin received within said first cut opening to separate said first cut opening into at least two distinct slots, said stabilizer pin establishing a size of each of said at least two distinct slots for making cuts in a bone.

2. The surgical instrumentation set as recited in claim 1, comprising a cutting tool configured to be inserted through said at least two distinct slots.

3. The surgical instrumentation set as recited in claim 2, wherein said cutting tool is a disposable cutting tool.

4. The surgical instrumentation set as recited in claim 1, wherein said bone preparation guide assembly includes a second cut guide connected to said first cut guide via a bridge, and said second cut guide includes a second cut opening configured to receive said stabilizer pin to separate said second cut opening into at least two additional distinct slots.

5. The surgical instrumentation set as recited in claim 1, comprising a slot that extends through said first cut guide adjacent to said first cut opening.

6. The surgical instrumentation set as recited in claim 5, comprising a distal proximal stylus having a post configured to extend through an opening of said slot.

7. The surgical instrumentation set as recited in claim 1, wherein said bone preparation guide assembly includes a second cut guide that extends generally perpendicular to said first cut guide.

8. The surgical instrumentation set as recited in claim 1, wherein said stabilizer pin includes a plug portion received within said first cut opening and a post portion that protrudes out of said first cut opening.

9. The surgical instrumentation set as recited in claim 1, comprising a second cut guide that extends transversely from said first cut guide, said second cut guide including a second cut opening, and said first cut opening and said second cut opening are configured to create cuts in a femur bone.

10. The surgical instrumentation set as recited in claim 9, wherein said first cut guide is a trochlear cut guide and said second cut guide is a distal cut guide.

11. The surgical instrumentation set as recited in claim 10, wherein said trochlear cut guide includes a slot for making additional cuts in said femur bone.

12. The surgical instrumentation set as recited in claim 10, wherein said distal cut guide includes a depth pin configured to establish a depth of said bone preparation guide assembly relative to an intercondylar notch of said femur bone.

13. The surgical instrumentation set as recited in claim 1, comprising a plurality of different osteotomes insertable through said bone preparation guide assembly to form said cuts in said bone.

14. The surgical instrumentation set as recited in claim 13, wherein at least one of said plurality of different osteotomes includes a depth control stop configured to control the depth of said cuts in said bone.

15. The surgical instrumentation set as recited in claim 1, comprising a slot extending through said first cut guide offset from said first cut opening, said slot including an opening configured to accommodate a distal proximal stylus.

16. The surgical instrumentation set as recited in claim 15, wherein said distal proximal stylus includes a handle and a post that extends from said handle.

17. The surgical instrumentation set as recited in claim 16, wherein said post is received through said opening of said slot to align said distal proximal stylus within an intercondylar notch of said bone.

18. A surgical instrumentation set, comprising:
a bone preparation guide assembly including:
a first cut guide including a first cut opening configured to receive a first cutting tool to form a first cut in a bone;
a second cut guide connected to said first cut guide and including a second cut opening configured to receive said first cutting tool to form a second cut in said bone; and a stabilizer pin insertable within at least said first cut opening to divide said first cut opening into at least two distinct slots, said at least two distinct slots configured to receive a second cutting tool to form angled cuts in said bone.

\* \* \* \* \*